(12) United States Patent
Aimi et al.

(10) Patent No.: US 7,722,552 B2
(45) Date of Patent: May 25, 2010

(54) GUIDE WIRE

(75) Inventors: Youki Aimi, Fujinomiya (JP); Yutaka Itou, Fujinomiya (JP); Hiraku Murayama, Fuji (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 176 days.

(21) Appl. No.: 10/892,326

(22) Filed: Jul. 16, 2004

(65) Prior Publication Data

US 2005/0038359 A1 Feb. 17, 2005

(30) Foreign Application Priority Data

Jul. 17, 2003 (JP) ............................. 2003-275953
Jun. 4, 2004 (JP) ............................. 2004-167575

(51) Int. Cl.
*A61B 5/00* (2006.01)

(52) U.S. Cl. .................................................... 600/585

(58) Field of Classification Search ................. 600/585, 600/433, 434
See application file for complete search history.

(56) References Cited

U.S. PATENT DOCUMENTS

| 4,538,622 | A | | 9/1985 | Samson et al. |
| 4,714,815 | A | | 12/1987 | Swarts et al. |
| 4,748,986 | A | * | 6/1988 | Morrison et al. ............. 600/585 |
| 4,934,380 | A | * | 6/1990 | de Toledo .................... 600/585 |
| 5,287,858 | A | * | 2/1994 | Hammerslag et al. ....... 600/585 |
| 5,372,144 | A | * | 12/1994 | Mortier et al. ............... 600/585 |
| 5,377,690 | A | * | 1/1995 | Berthiaume .................. 600/585 |
| 5,429,139 | A | | 7/1995 | Sauter |
| 5,640,970 | A | * | 6/1997 | Arenas ........................ 600/585 |
| 5,666,969 | A | | 9/1997 | Urick et al. |
| 5,807,279 | A | | 9/1998 | Viera |
| 5,876,356 | A | * | 3/1999 | Viera et al. .................. 600/585 |
| 5,876,783 | A | | 3/1999 | Dobson |
| 5,891,055 | A | | 4/1999 | Sauter |
| 5,951,496 | A | | 9/1999 | Willi |
| 6,001,068 | A | | 12/1999 | Uchino et al. |
| 6,602,207 | B1 | * | 8/2003 | Mam et al. ................... 600/585 |
| 6,884,225 | B2 | * | 4/2005 | Kato et al. ................... 600/585 |
| 7,182,735 | B2 | * | 2/2007 | Shireman et al. ............ 600/585 |
| 2003/0125642 | A1 | | 7/2003 | Kato et al. |
| 2003/0181828 | A1 | * | 9/2003 | Fujimoto et al. ............. 600/585 |

(Continued)

FOREIGN PATENT DOCUMENTS

EP 0 803 266 A 10/1997

(Continued)

*Primary Examiner*—Max Hindenburg
*Assistant Examiner*—Helen Nguyen
(74) *Attorney, Agent, or Firm*—Buchanan Ingersoll & Rooney PC

(57) ABSTRACT

A guide wire comprises a core member, and a coil covering at least a distal end side portion of the core member. The guide wire comprises a coil fixing member which is fixed to the distal end side portion of the core member and which is adapted to fix the coil concentrically with the core member at an intermediate portion in the longitudinal direction of the coil, with the coil being fixed to the coil fixing member. The coil can be disposed concentrically with the core member, with the distal end portion of the guide wire undergoing generally uniform favorable deformations at the time of insertion into a living body, thus providing relatively excellent operationality.

20 Claims, 18 Drawing Sheets

U.S. PATENT DOCUMENTS

| | | | |
|---|---|---|---|
| 2003/0197503 A1 * | 10/2003 | Kawano et al. | 324/207.21 |
| 2004/0064069 A1 | 4/2004 | Reynolds et al. | |
| 2004/0167442 A1 | 8/2004 | Shireman et al. | |
| 2004/0167443 A1 | 8/2004 | Shireman et al. | |
| 2005/0145307 A1 | 7/2005 | Shireman et al. | |

FOREIGN PATENT DOCUMENTS

| | | |
|---|---|---|
| JP | 2002-336360 A | 11/2002 |
| WO | WO 02/05886 A | 1/2002 |

* cited by examiner

GUIDE WIRE

This application is based on and claims priority under 35 U.S.C. §119 with respect to Japanese Application No. 2003-275953 filed on Jul. 17, 2003 and Japanese Application No. 2004-167575 filed on Jun. 4, 2004, the entire content of both of which is incorporated herein by reference.

FIELD OF THE INVENTION

The present invention generally relates to a guide wire. More particularly, the invention pertains to a guide wire for use in introducing a catheter into a body lumen such as a blood vessel.

BACKGROUND DISCUSSION

Guide wires are used to guide a catheter in treatment of sites at which open surgery is difficult or which require or benefit from low invasiveness to the living body, for example PTCA (Percutaneous Transluminal Coronary Angioplasty), or in examination such as cardioangiography. A guide wire used in the PTCA procedure is inserted, with its distal end protruding from the distal end of a balloon catheter, into the vicinity of a target angiostenosis portion together with the balloon catheter, and is operated to guide the distal end portion of the balloon catheter to the vicinity of the angiostenosis portion.

Since blood vessels are curved in a relatively complicated manner, a guide wire used to insert a balloon catheter into a blood vessel is required to have various characteristics such as appropriate flexibility and resiliency against bending, pushability and transmission performance (generically called "operationality") for torque transmissibility at the proximal end portion to the distal end side, and kink resistance (resistance against sharp bending).

To obtain appropriate flexibility as one of the above-mentioned characteristics, there has been known a guide wire in which a metallic coil having flexibility against bending is provided around a small-diameter core member at the distal end of the guide wire, or a guide wire including a core member made of a superelastic material such as an Ni—Ti alloy for imparting flexibility and resiliency.

The known guide wires of the former type, comprising the coil, include a guide wire in which two coils made of different materials are disposed in series and are fixed to a core member in a mutually screw-engaged state, as disclosed in U.S. Pat. No. 4,538,622. In fixing the coils and the core member of the guide wire to each other, however, it has not always been easy to fix the core member in the center of the coils.

To address this problem, U.S. Pat. No. 5,951,496 discloses a guide wire produced by a method in which two coils are coupled on a centering mold, with the mold thereafter being removed. In addition, U.S. Pat. No. 5,429,139 discloses a guide wire in which two coils are connected to each other through a joint coil. Further, U.S. Pat. No. 5,666,969 discloses a guide wire in which two coils are coupled through a spacer.

Joining the two coils to the core member according to U.S. Pat. No. 4,538,622, the solder would flow in the space between the coils and the core member so that the joint portion would have a relatively large length in the axial direction. Besides, in the methods of coupling the two coils on a mold or joint coil according to U.S. Pat. Nos. 5,951,496 and 5,429,139, though the offset between the coils on the axis is reduced, there is the problem that the operation is intricate and that there would be an offset between the center axis of the coils and the center axis of the core member in connecting the coupled coils to the core member. Furthermore, although the spacer according to U.S. Pat. No. 5,666,969 has a radiopaque performance and other characteristic features, the publication includes no implication about the offset between the coils and the offset between the coils and the core member.

SUMMARY

According to one aspect, a guide wire comprises a core member, and a coil covering at least a distal end side portion of the core member. The guide wire comprises a coil fixing member which is fixed to the distal end side portion of the core member and which is adapted to fix the coil concentrically with the core member at least at a portion in the longitudinal direction of the coil, with the coil being fixed to the coil fixing member.

In accordance with another aspect, a guide wire comprises a core member having a distal end side portion, and a coil covering at least the distal end side portion of said core member and comprising a distal end side coil and a proximal end side coil. The distal end side coil and the proximal end side coil possess different inside diameters. A coil fixing member is fixed to the distal end side portion of the core member to fix the coil with the core member at least at a portion in a longitudinal direction of the coil. The coil fixing member comprises a smaller diameter portion and a larger diameter portion corresponding to a difference in inside diameter between the distal end side coil and the proximal end side coil.

Another aspect involves a guide wire comprising a core member having a distal end side portion, and a coil covering at least the distal end side portion of the core member, with the coil being formed of a material possessing a melting point. A fixing member is fixed to the distal end side portion of the core member, and is formed of a material possessing a melting point that is lower than the melting point of the material forming the coil. In addition, the coil is fixed to the coil fixing member by welding.

BRIEF DESCRIPTION OF THE DRAWING FIGURES

DETAILED DESCRIPTION

Referring initially to FIGS. 1-9, the guide wire 1 according to one disclosed embodiment comprises a core member 2 and a coil 3 covering at least a distal end side portion of the core member 2. The guide wire 1 also comprises a coil fixing member 4 which is fixed to the distal end side portion of the core member 2. The coil fixing member 4 is adapted to fix the coil 3 concentrically with the core member 2 at least at a portion in the longitudinal direction of the coil 3, and the coil 3 is fixed to the coil fixing member 4 through an adhesion material.

Figure 1:
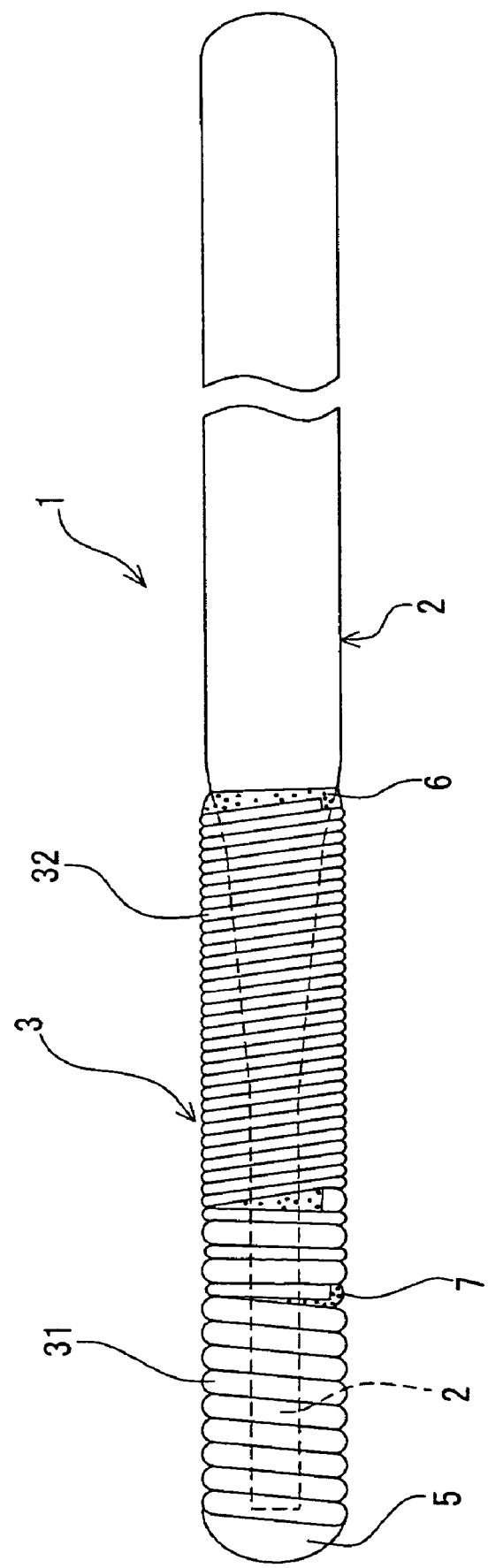
FIG. 1 is a partly omitted front view of one embodiment of the guide wire according to the present invention.
Figure 2:
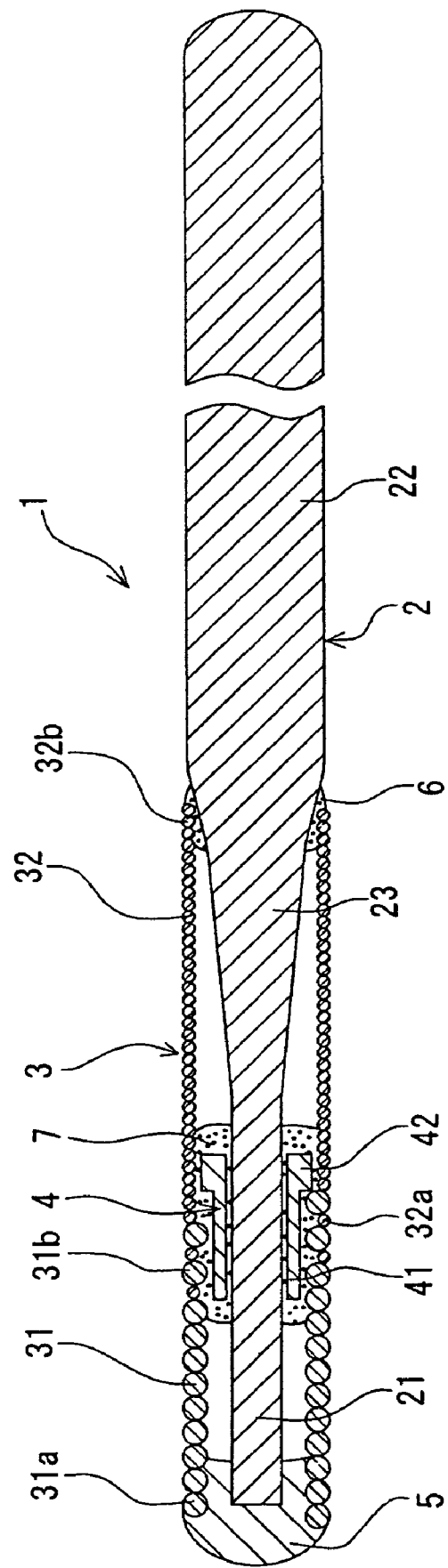
FIG. 2 is a partly omitted sectional view of the guide wire shown in FIG. 1.

The guide wire 1 according to the embodiment shown in FIGS. 1 and 2 comprises the core member 2, and the coil 3 covering at least a distal end side portion of the core member 2. The coil 3 comprises a distal end side coil 31 and a proximal end side coil 32. As shown in FIG. 2, the coil fixing member 4 fixes the proximal end portion 31b of the distal end side coil 31 and a distal end portion 32a of the proximal end side coil 32 to the core member 2. In this embodiment, the distal end 31a of the distal end side coil 31 is fixed to a distal end portion of the core member 2. The proximal end of the coil 3, in this embodiment the proximal end 32b of the proximal end side coil 32, is fixed to a portion of the core member 2 on the proximal end side relative to the distal end of the core member 2 by a predetermined distance. That is, in this version of the guide wire 1, the distal end of the coil 3 is fixed to the distal end of the core member 2, the proximal end of the coil 3 is fixed to the portion of the core member 2 that is at the proximal end side of the distal end of the core member 2 by the predetermined distance. The core member 2 constitutes a main body portion of the guide wire 1 extending from a proximal end portion of the coil 3.

The whole length of the guide wire 1 is preferably about 300 mm to 4500 mm, more preferably about 1000 mm to 2000 mm.

The core member 2 comprises a main body portion 22, a tapered portion 23, and a distal end portion 21, arranged in this order from the proximal end side. The main body portion 22 is an elongate portion having a substantially constant outside diameter and extending toward the distal end side from the proximal end of the core member 2. The distal end portion 21 of the core member is smaller in diameter than the main body portion 22. In this embodiment, the distal end portion 21 extends toward the distal end side while having a substantially constant diameter. The tapered portion 23 is formed between the distal end portion 21 and the main body portion 22.

The outside diameter of the guide wire 1 at the main body portion 22 is preferably about 0.2 mm to 1.8 mm, more preferably about 0.3 mm to 1.6 mm. The outside diameter of the distal end portion 21 is about 0.05 mm to 1.6 mm, and the length of the distal end portion 21 is 10 mm to 500 mm, preferably 20 mm to 300 mm. The distal end portion 21 may be more flexible on the distal end side. For example, the distal end portion 21 may be heat treated to have a flexibility that gradually increases as the distal end is approached.

Examples of the material used to constitute the core member 2 include various metallic materials such as superelastic alloys (e.g., Ni—Ti based alloy), stainless steels, piano wire, etc.

The whole length of the coil 3 is 10 mm to 500 mm, preferably 20 mm to 300 mm, and the outside diameter of the coil 3 is 0.2 mm to 1.8 mm, preferably 0.3 mm to 1.6 mm. In this illustrated embodiment, the coil 3 covers the distal end portion 21 and the tapered portion 23 of the core member 2. The distal end of the coil 3 is fixed to the distal end of the core member 2, and the proximal end of the coil 3 is attached to a proximal end portion of the tapered portion 23 of the core member 2 through a brazing metal 6 or the like.

As mentioned above, this embodiment shown in FIGS. 1 and 2 comprises the coil 3 composed of the distal end side coil 31 and the proximal end side coil 32. Further, the proximal end portion 31b of the distal end side coil 31 and the distal end portion 32a of the proximal end side coil 32 are entangled with each other and overlap one another in the axial direction as shown in FIG. 2. The entanglement of the two coils 31, 32 prevents them from being spaced away from each other. The distance over which the coils 31, 32 are entangled with each other is preferably about 0.1 mm to 2 mm.

In addition, the distal end side coil 31 and the proximal end side coil 32 preferably have different physical properties. The physical properties of the two coils 31, 32 can be variously selected according to the purpose of the guide wire. For example, the distal end side coil 31 may be more flexible than the proximal end side coil 32 (the flexibility of the coil can be changed, for example, by winding the coil with or without a gap between adjacent turns of the elementary wire, by varying the diameter of the elementary wire of the coil, or by changing the material of the coil). The distal end side coil 31 may be higher in radiopaque property than the proximal end side coil 32. In this embodiment, the gap between adjacent turns of the elementary wire of the distal end side coil 31 is larger than the gap between adjacent turns of the elementary wire of the proximal side coil 32. Furthermore the diameter of the elementary wire of the distal end side coil 31 is larger than the diameter of the elementary wire of the proximal end side coil 32. In the illustrated embodiment here, the distal end side coil 31 and the proximal end side coil 32 have nearly equal outside diameters. The length of the distal end side coil 31 is preferably about 3 mm to 60 mm, and the length of the proximal end side coil 32 is preferably about 10 mm to 40 mm. In this embodiment, the inside diameter of the distal end side coil 31 is smaller than the inside diameter of the proximal end side coil 32.

Examples of the material used to constitute the coil include superelastic alloys (e.g., Ni—Ti based alloy), stainless steels, and noble metals such as gold and platinum. The distal end side coil 31 and the proximal end side coil 32 may be either formed of the same material or formed of different materials. Where different materials are used, it is possible, for example, to use a noble metal such as gold and platinum for the distal end side coil 31 and a stainless steel for the proximal end side coil 32, or to use a superelastic alloy for the distal end side coil 31 and a stainless steel for the proximal end side coil 32.

The distal end of the coil 3 is fixed to the distal end of the core member 2 through a brazing metal 5. The distal end of the guide wire 1 formed of the brazing metal 5 constitutes or provides a hemispherical distal end portion. The hemispherical distal end means that the distal end is formed in the shape of a substantially curved surface, inclusive of a hanging bell-like shape, a bullet-like shape and the like.

The coil fixing member 4 is fixed to a distal end portion of the core member 2. The fixation of the fixing member 4 to the core member 2 may be carried out by any method such as fitting and brazing. The fixing member 4 is adapted to fix the coil 3 concentrically with the core member 2 at least at a portion in the longitudinal direction of the coil 3. The length of the fixing member 4 is preferably about 0.2 mm to 1.0 mm.

In this embodiment, the position of the fixing member 4 in the coil 3 is located on the distal end side of the coil relative to a middle portion in the longitudinal direction of the coil 3. However, the fixing member 4 may be located nearly at the middle portion in the longitudinal direction of the coil 3, or may be located on the proximal end side relative to the middle portion of the coil in the longitudinal direction of the coil 3. The position of the fixing member 4 in the coil 3 is such that it is spaced by a predetermined distance from the distal end or the proximal end of the coil 3. In addition, a plurality of such fixing members 4 may be provided. For example, the fixing members 4 may be disposed at positions respectively on the distal end side and on the proximal end side by a predetermined distance from the joint portion between the distal end side coil 31 and the proximal end side coil 32, and the distal end side coil 31 may be fixed to the distal end side fixing member, and the proximal end side coil 32 to the proximal end side fixing member, through an adhesion material such as a brazing metal.

Figure 3:
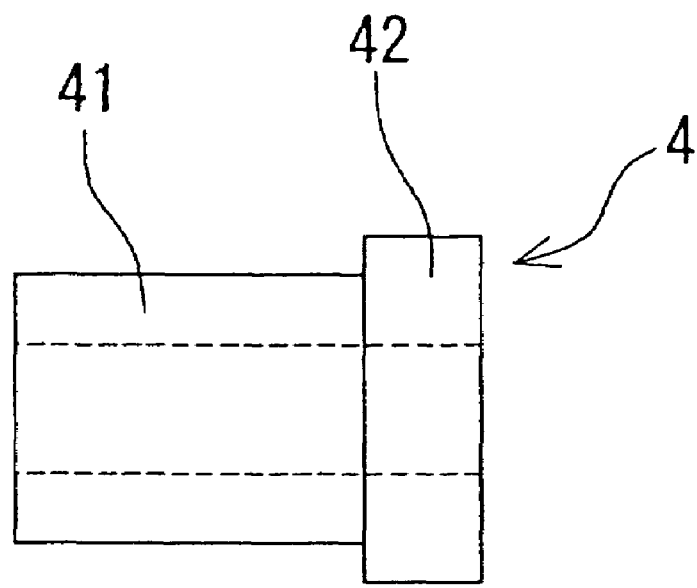
FIG. 3 is a front view of one example of a coil fixing member used in the guide wire.
Figure 4:
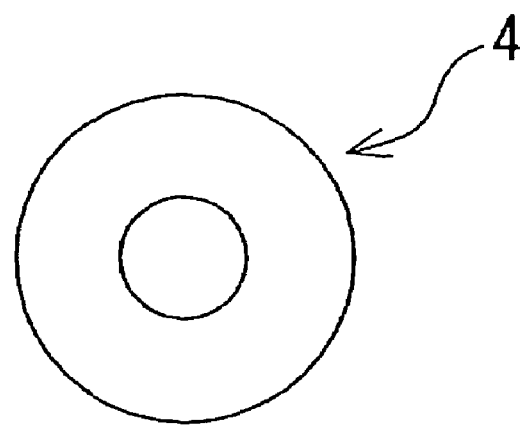
FIG. 4 is a right side view of the coil fixing member shown in FIG. 3.

In the guide wire 1 according to this embodiment, the fixing member is a tubular member, as shown in FIGS. 2-4. The fixing member 4 comprises a smaller diameter portion 41 corresponding in position to a proximal end portion of the distal end side coil 31, in this embodiment, to the entangled portion of the distal end side coil 32 and the proximal end side coil 32, and a larger diameter portion 42 corresponding in position to a portion of the proximal end side coil 32 as illustrated in FIG. 2. In this guide wire 1, the fixing member 4 is provided at the position of the entangled portion of the distal end side coil 31 and the proximal end side coil 32. The outside diameter of the smaller diameter portion 41 of the fixing member 4 is slightly smaller than the inside diameter of the distal end side coil 31. The outside diameter of the large diameter portion 42 of the fixing member 4 is slightly smaller than the inside diameter of the proximal end side coil 32. In addition, the outside diameter of the larger diameter portion 42 of the fixing member 4 is preferably slightly larger than the inside diameter of the distal end side coil 31. This helps ensure that, as shown in FIG. 2, the proximal end of the distal end side coil 31 abuts on an end portion of the larger diameter portion 42 of the fixing member 4 so that the distal end side coil 31 can be inhibited or prevented from moving. Furthermore, the operation of fixing the coil 3 to the core member 2 is facilitated. In this version of the fixing member 4, the axial length of the larger diameter portion 42 is smaller than the axial length of the smaller diameter portion 41.

The coil 3 can be fixed to the coil fixing member 4 by a brazing metal 7 used as an adhesion material. Examples of the adhesion material include resin-made adhesives, other than the above-mentioned brazing metal (inclusive of solder). The coil 3 is fixed to the coil fixing member 4 through the adhesion material. The adhesion material can be disposed to fill the gap between the fixing member 4 and the core member 2.

With such a fixing member 4 provided, the gap between the core member 2 (fixing member 4) and the coil 3 is reduced, so that the coil 3 can be fixed concentrically with the core member 2, and, at the time of insertion into a living body, the distal end portion of the guide wire 1 undergoes uniform favorable deformations, with a relatively smooth torque transmissibility being realized. In addition, the brazing metal is prevented from excessively flowing in the axial direction of the guide wire 1 at the time of fixation, so that the length of the fixation portion between the coil 3 and the core member 2 can be made smaller.

Examples of the material of the coil fixing member 4 include not only metallic materials, e.g., noble metals such as gold and copper, which are well compatible with the brazing metal (solder), e.g., silver solder, and stainless steels, but also plastics. Where the coil fixing member 4 is formed of a plastic, the adhesion material is preferably an adhesive for resins.

Figure 5:
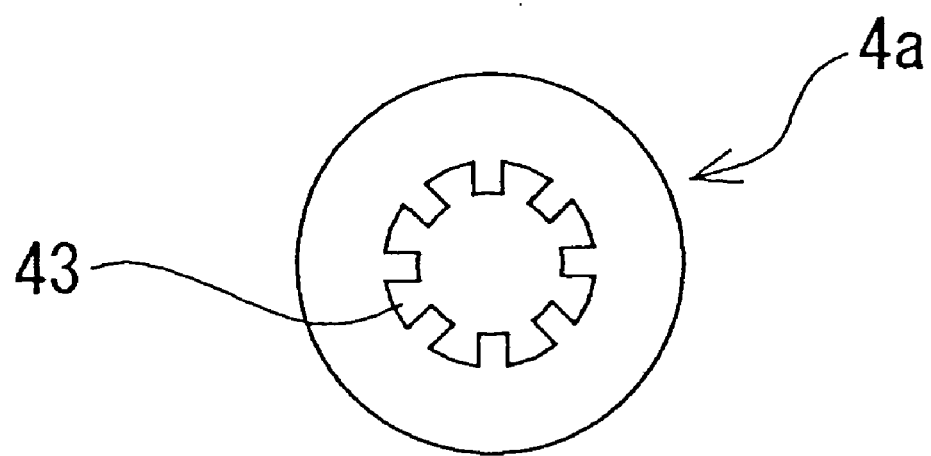
FIG. 5 is a right side view of another example of the coil fixing member used in the guide wire.

The coil fixing member 4 is not limited to that in the above-described embodiment. For example, a fixing member 4a such as shown in FIG. 5 can be employed. Here, the inside wall of the lumen is provided with a groove or grooves 43 extending in the axial direction. It is preferable that a plurality of grooves 43 be provided as illustrated. The grooves can help facilitate the flow of the brazing metal into the gap between the fixing member and the core member.

Figure 6:
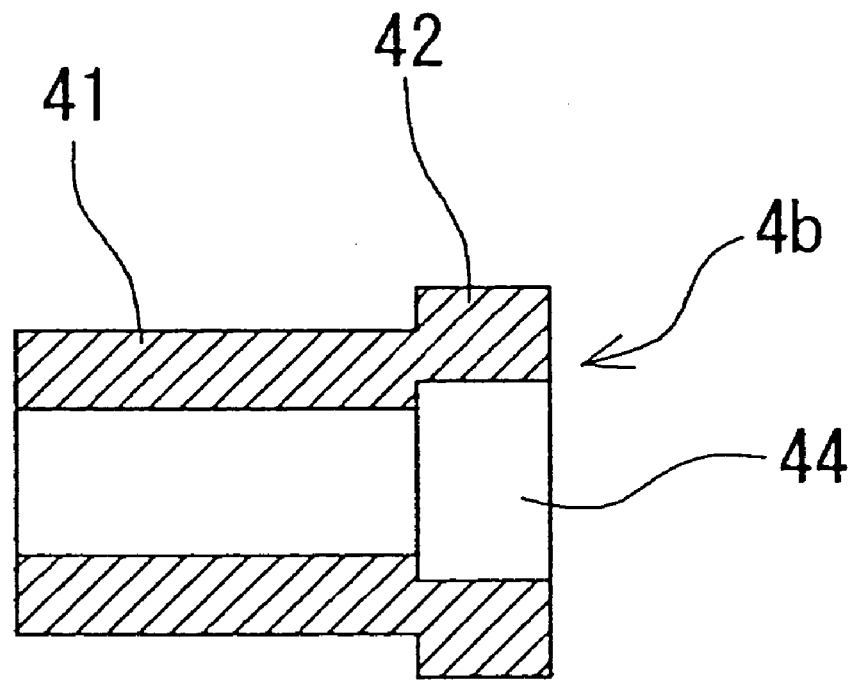
FIG. 6 is a sectional view of another example of the coil fixing member used in the guide wire.

In addition, a fixing member 4b such as shown in FIG. 6 may be employed. Here, the lumen at the portion of the large diameter portion 42 is a portion 44 having an enlarged inside diameter as compared with other portions of the fixing member. This enlarged inside diameter portion 44 can help facilitate the flow of the brazing metal into the gap between the fixing member and the core member.

Figure 7:
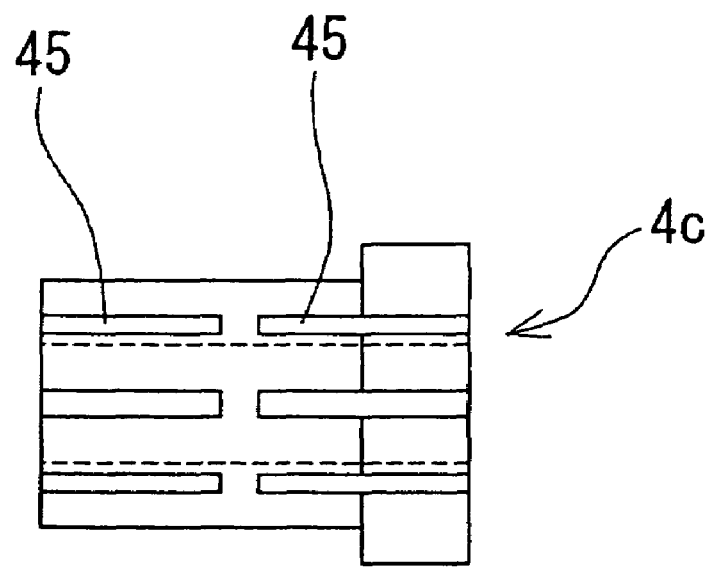
FIG. 7 is a front view of a further example of the coil fixing member used in the guide wire.

As a further example, a fixing member 4c such as shown in FIG. 7 can be adopted. In this version, the fixing member is provided with a slot or slots 45 extending in the axial direction. It is preferable that a plurality of slots 45 be provided as shown. In the fixing member 4c shown in FIG. 7, the slots 45 do not communicate with each other over the range from one end to the other end of the fixing member. That is, one set of slots extends from the distal end of the fixing member toward the proximal end, while another set of slots extend from proximal end toward the distal end, with the slots in one set stopping short of the slots in the other set. The slots help facilitate the flow of the brazing metal into the gap between the fixing member and the core member and also facilitate the flow of the brazing metal into the gap between the fixing member and the coil.

Figure 8:
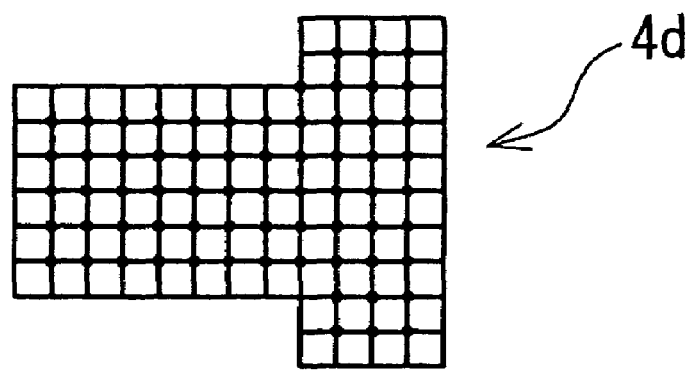
FIG. 8 is a front view of yet another example of the coil fixing member used in the guide wire.
Figure 9:
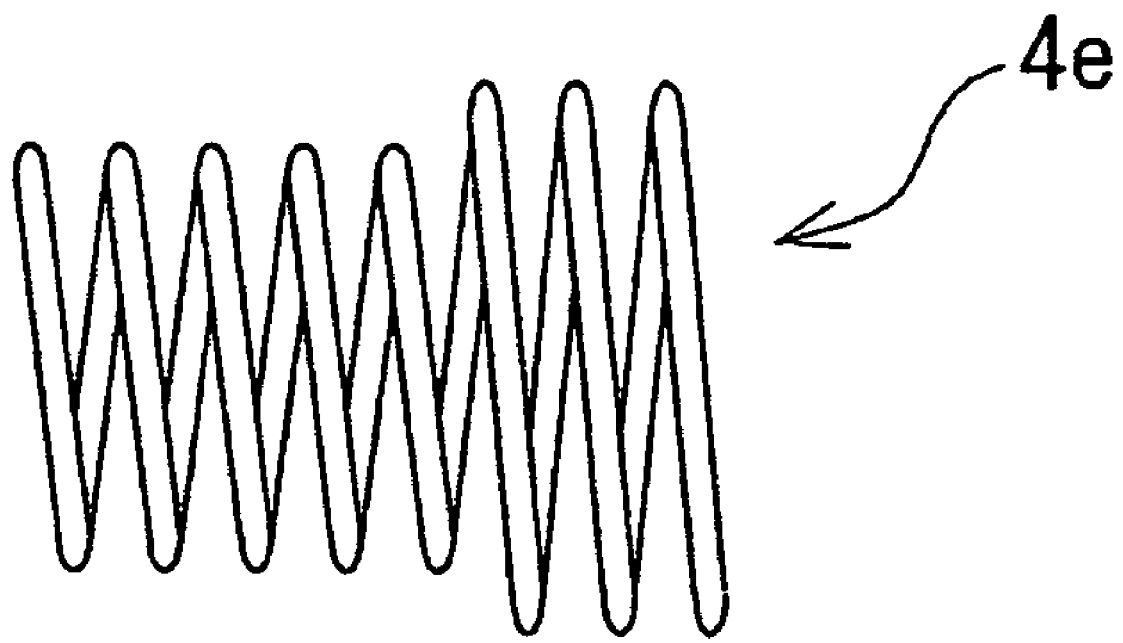
FIG. 9 is a front view of a still further example of the coil fixing member used in the guide wire.

FIGS. 8 and 9 illustrate additional versions of the fixing member that can be employed. The fixing member 4d shown in FIG. 8 is a net-like body, while the fixing member 4e shown in FIG. 9 is a coil-like member. These fixing members also help facilitate the flow of the brazing metal into the gap between the fixing member and the core member and help facilitate the flow of the brazing metal into the gap between the fixing member and the coil.

In addition, it is preferable that the fixing member covers the entire circumference of a portion of the core member, but it is possible to utilize a fixing member which does not cover a part or parts of the core member as in the case of, for example, the fixing members provided with slots in the axial direction. Furthermore, the fixing member may be composed of a plurality of members in cross-section thereof, for example the fixing member may be composed of two or more members for covering the periphery of the core member, while having at least one non-covering portion.

Figure 10:
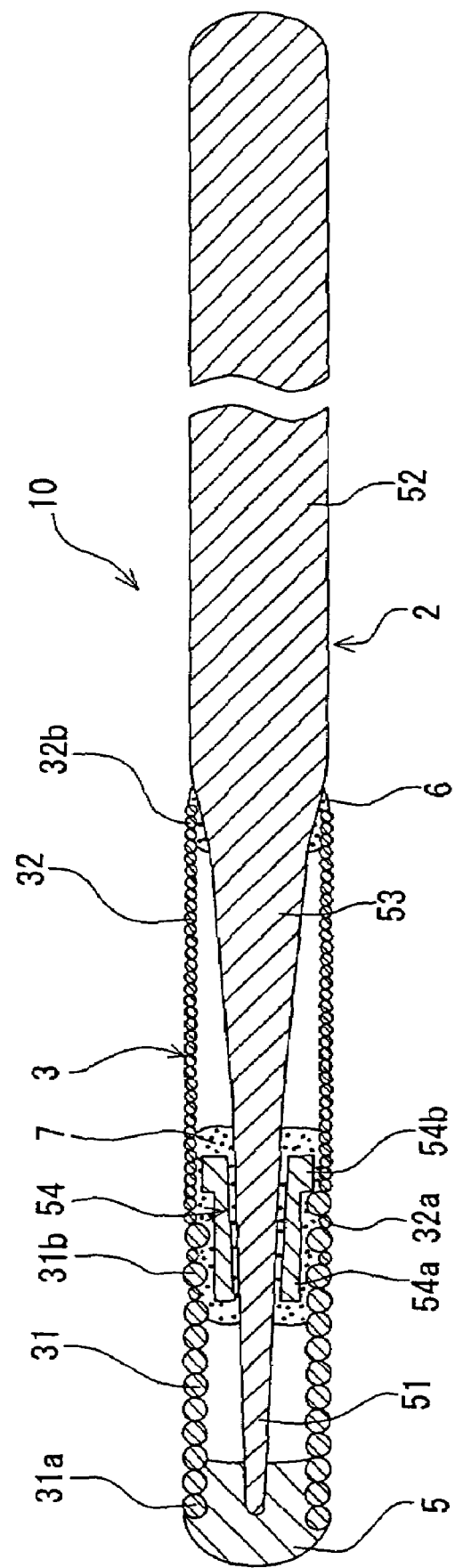
FIG. 10 is a partly omitted sectional view of another embodiment of the guide wire.

A guide wire 10 according to another embodiment is shown in FIG. 10. This version of the guide wire 10 is fundamentally similar to the above-described guide wire 1. The differences between this embodiment and the earlier described embodiment pertain to the form of the distal end portion of the core member and the form of the lumen of the coil fixing member. The portions of the guide wire that are similar to those already described above will not be repeated. Rather, the following discussion is directed primarily to a discussion of the differences of this version relative to the earlier described embodiment.

The core member 2 comprises a main body portion 52, a tapered intermediate portion 53, and a tapered distal end portion 51, arranged in this order from the proximal end side. The main body portion 52 is an elongate portion having a nearly constant outside diameter which extends toward the distal end side from the proximal end of the core member 2. The tapered distal end portion 51 is smaller in diameter than the main body portion 52 and gradually decreases in diameter approaching the distal end. The tapered intermediate portion 53 is formed between the tapered distal end portion 51 and the main body portion 52. The tapered intermediate portion 53 has a taper which varies in outside diameter to a greater extent than the taper of the tapered distal end portion 51. This helps ensure that the distal end portion 51 is more flexible on the distal end side. It is to be noted that the configuration of the tapered distal end portion 51 is not limited to being tapered over the entire length thereof, but may be configured so that it partly has a straight portion.

In the guide wire 10 according to this embodiment, the fixing member is a tubular member as shown in FIG. 10. In addition, the lumen of the fixing member 54 is decreased in diameter toward the distal end of the fixing member, according to the taper shape of the distal end portion of the core member. Therefore, when the fixing member 54 is mounted to the core member 2, the fixing member 54 itself can be easily disposed concentrically with the core member 2, without jouncing. Like the above-described fixing member 4, the fixing member 54 shown in FIG. 10 comprises a smaller diameter portion 54*a* corresponding in position to the entangled portion of the distal end side coil and the proximal end side coil, and a larger diameter portion 54*b* corresponding in position to a portion of the proximal end side coil as shown. In this guide wire 10 also, the fixing member 54 is provided at the position of the entangled portion of the distal end side coil 31 and the proximal end side coil 32. The outside diameter of the smaller diameter portion 54*a* of the fixing member 54 is slightly smaller than the inside diameter of the distal end side coil 31. The outside diameter of the larger diameter portion 54*b* of the fixing member 54 is slightly smaller than the inside diameter of the proximal end side coil 32. In addition, the outside diameter of the larger diameter portion 54*b* of the fixing member 54 is preferably slightly larger than the inside diameter of the distal end side coil 31. This helps ensure that the rear end of the distal end side coil 31 abuts on an end portion of the larger diameter portion 54*b* of the fixing member 54 as shown in FIG. 10. The coil 3 can be fixed to the coil fixing member 54 by a brazing metal 7. The fixing member 54 configured in the illustrated manner helps reduce the gap between the core member (fixing member) and the coil, so that the coil 3 can be fixed concentrically with the core member, and a distal end portion of the guide wire undergoes generally uniform favorable deformations at the time of insertion into a living body.

Figure 11:
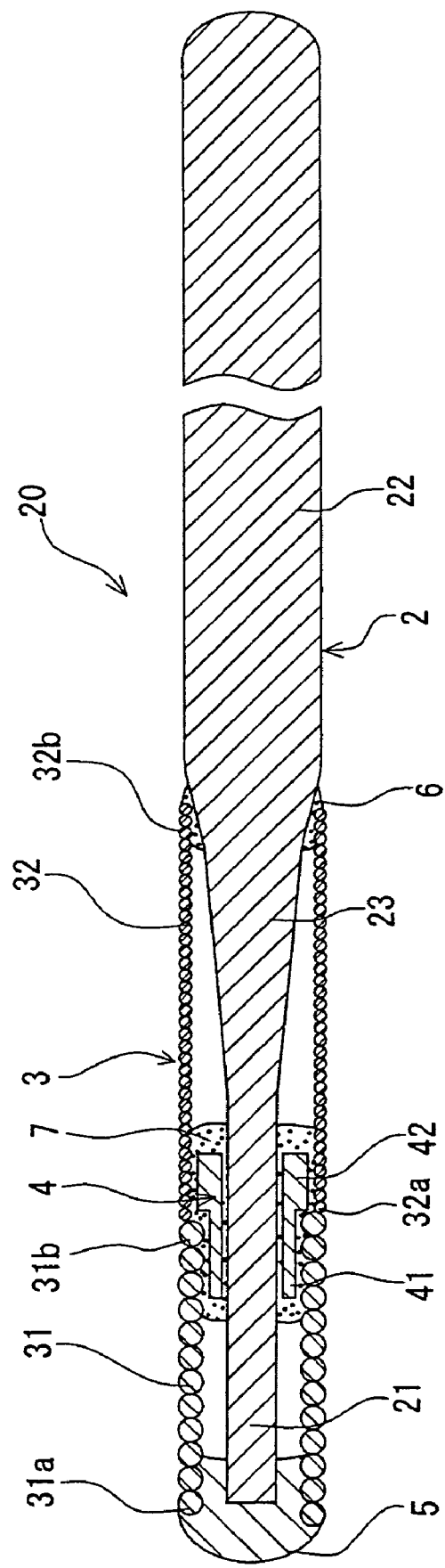
FIG. 11 is a partly omitted sectional view of a further embodiment of the guide wire.

FIG. 11 illustrates another embodiment of the guide wire. This version of the guide wire 20 is fundamentally similar to the above-described guide wire 1. The differences between this embodiment and the earlier described embodiment involve the proximal end portion 31*b* of the distal end side coil 31 and the distal end portion 32*a* of the proximal end side coil 32, which comprise the coil 3, not being entangled with each other. The portions of this version of the guide wire that are similar to those already described above will not be repeated. Rather, the following discussion is directed primarily to a discussion of the differences of this version relative to the earlier described embodiment of the guide wire 1.

Since the proximal end portion 31*b* of the distal end side coil 31 and the distal end portion 32*a* of the proximal end side coil 32 are not entangled with each other, the coil fixing member 4 is a member which fixes the proximal end portion 31*b* of the distal end side coil 31 and the distal end portion 32*a* of the proximal end side coil 32 to the core member 2. Therefore, the fixing member 4 functions to fix both the distal end side coil 32 and the proximal end side coil 32, individually, concentrically with the core member 2. The fixing member 4 comprises a smaller diameter portion 41 and a larger diameter portion 42, with the outside diameter of the smaller diameter portion 41 being slightly smaller than the inside diameter of the distal end side coil 31. The outside diameter of the larger diameter portion 42 of the fixing member 4 is slightly smaller than the inside diameter of the proximal end side coil 32. In addition, the outside diameter of the larger diameter portion 42 of the fixing member 4 is preferably slightly greater than the inside diameter of the distal end side coil 31. This helps ensures that the rear end of the distal end side coil 31 abuts on an end portion of the larger diameter portion 42 of the fixing member 4 as shown in FIG. 11. The coil 3 can be fixed to the coil fixing member 4 by a brazing metal 7. This fixing member 4 helps reduce the gap between the core member (fixing member) and the coil, so that the coil 3 can be fixed concentrically with the core member, and the distal end portion of the guide wire 20 undergoes generally uniform favorable deformations at the time of insertion into a living body.

Figure 12:
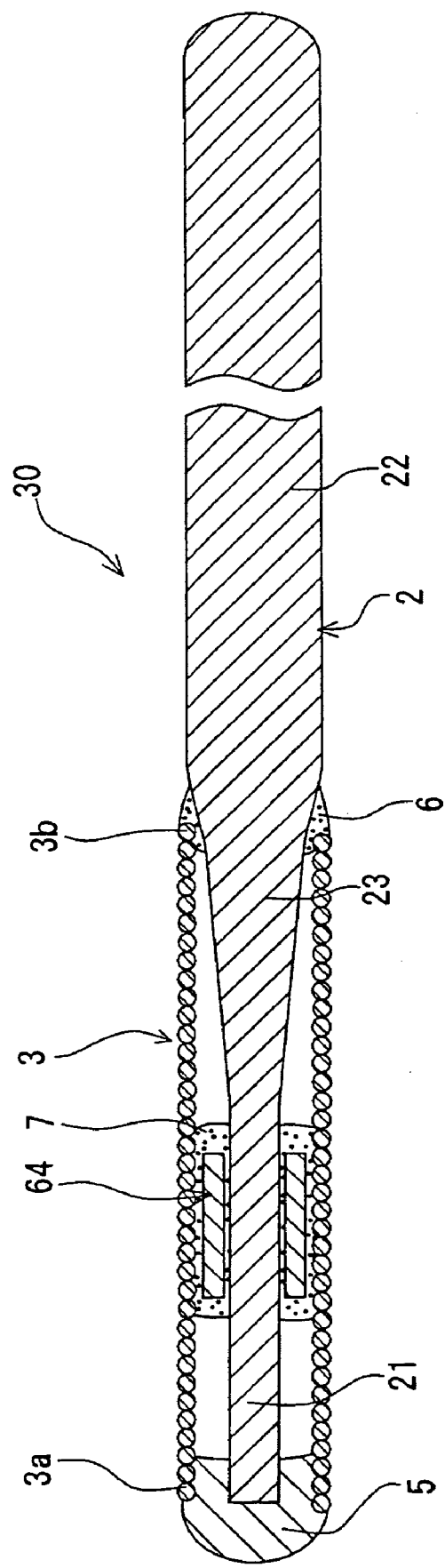
FIG. 12 is a partly omitted sectional view of yet another embodiment of the guide wire.

FIG. 12 illustrates yet another embodiment of the guide wire. This version of the guide wire 30 is fundamentally similar to the above-described guide wire 1. The differences between this embodiment of the guide wire and the earlier described embodiment reside primarily in the use of a single-element coil as the coil 3 and the form of the coil fixing member. Thus, the description which follows will identify primarily the differences between this version of the guide wire and the earlier described embodiment.

As shown in FIG. 12, the coil 3 is entirely formed from the same elementary wire, and the coil 3 as a whole has substantially the same outside diameter and the same inside diameter. The coil fixing member 64 is a tubular member having substantially the same outside diameter (i.e., a constant outside diameter) as shown in FIG. 12. With this configuration of the fixing member 64, an intermediate portion of the coil 3 can be fixed concentrically with the core member. The outside diameter of the fixing member 64 is slightly smaller than the inside diameter of the coil 3. The coil 3 is fixed to the coil fixing member 64 by a brazing metal 7. This fixing member 64 helps reduce the gap between the core member (fixing member) and the coil, so that the coil 3 can be fixed concentrically with the core member, and the distal end portion of the guide wire 30 undergoes generally uniform favorable deformations at the time of insertion into a living body.

The single-element coil includes not only the coil entirely formed of the same material but also a coil in which the elementary wire on the distal end side is formed of a radiopaque material such as platinum, whereas the elementary wire on the proximal end side is formed of a material lower in radiopaque property than that on the distal end side, for example a stainless steel or the like, and a proximal end portion of the distal end side elementary wire and a distal end portion of the proximal end side elementary wire are joined to each other so as to obtain an integral coil. In this case, the fixing member 64 may be interposed between the core member and the coil in the same manner as above-described, at the joint portion between the elementary wires, or may be located on the distal end side and/or the proximal end side relative to the joint portion.

Figure 13:
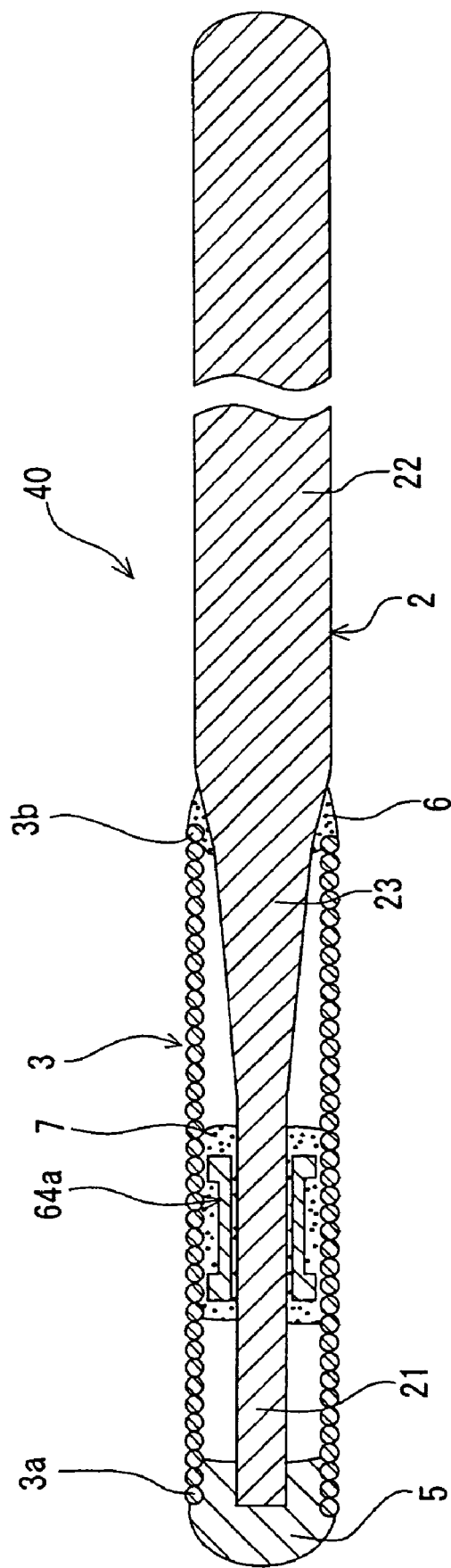
FIG. 13 is a partly omitted sectional view of a still further embodiment of the guide wire.

In addition, a guide wire 40 such as shown in FIG. 13 may be employed in which a coil fixing member 64a is provided at its outside surface with a groove or grooves extending in the axial direction or an annular groove or grooves. This helps facilitate the flow of a brazing metal into the gap between the coil 3 and the fixing member 64a.

In the embodiments shown in FIGS. 12 and 13, a gap is provided near the coil 3 located over the coil fixing member 64, whereby melting-in of the brazing metal (solder) via the gap can be facilitated.

It is to be understood that the guide wires 20, 30 according to the above-described embodiments may also have the form of the distal end portion of the core member and the form of the lumen of the coil fixing member which are the same as in the above-described guide wire 10.

Figure 14:
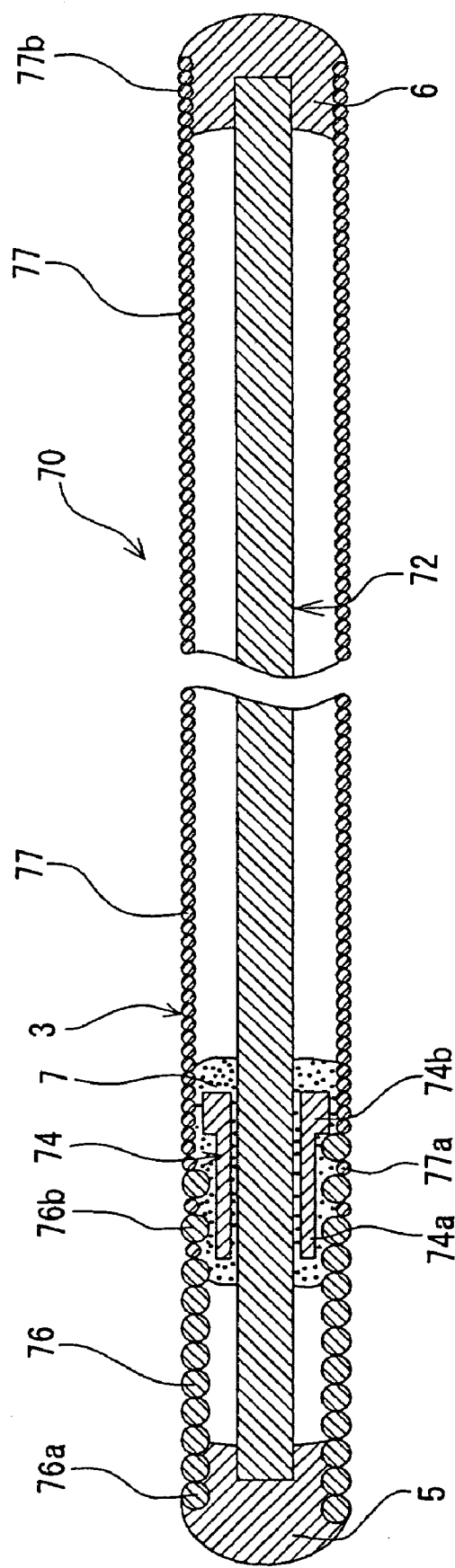
FIG. 14 is a partly omitted sectional view of a yet further embodiment of the guide wire.

FIG. 14 illustrates yet another embodiment of the guide wire. This version of the guide wire 70 shown in FIG. 14 is fundamentally similar to the embodiment of the guide wire 1 described above. The differences between this embodiment and the earlier described embodiment lie primarily in the form of the core member and the form of the coil. The description which follows will discuss primarily the differences associated with this embodiment and a description of other aspects of the guide wire will not be repeated.

As shown in FIG. 14, the coil 3 covers the whole part of or the entire longitudinal extent of the core member 72. The core member 72 has substantially the same outside diameter over the range from the proximal end side to the distal end side. However, the distal end portion of the core member 72 may be decreased in diameter toward the distal end in the same manner as in the above-described guide wire 10.

The coil 3 comprises a distal end side coil 76 and a proximal end side coil 77. The distal end side coil 76 is the same as the above-described distal end side coil 31. The proximal end side coil 77 has its rear end 77b extending to the rear end of the core member 72 and fixed to the rear end of the core member 72. In the guide wire 70 according to this embodiment a proximal end portion 76b of the distal end side coil 76 and a distal end portion 77a of the proximal end side coil 77 overlap one another and are entangled with each other in the same manner as described above in connection with the guide wire shown in FIG. 2. A fixing member 74 comprises a smaller diameter portion 74a corresponding in position to the entangled portion of the distal end side coil 76 and the proximal end side coil 77, and a larger diameter portion 74b corresponding in position to a portion of the proximal end side coil 77 as shown in FIG. 14. Thus, in this guide wire 70, the fixing member 74 is provided at the position of the entangled portion of the distal end side coil 76 and the proximal end side coil 77.

The outside diameter of the smaller diameter portion 74a of the fixing member 74 is slightly smaller than the inside diameter of the distal end side coil 76. The outside diameter of the larger diameter portion 74b of the fixing member 74 is slightly smaller than the inside diameter of the proximal end side coil 77. In addition, the outside diameter of the larger diameter portion 74a of the fixing member 74 is preferably slightly larger than the inside diameter of the distal end side coil 76. This helps ensure that the rear end of the distal end side coil 76 abuts on an end portion of the larger diameter portion 74b of the fixing member 74.

The coil 3 is fixed to the coil fixing member 74 with a brazing metal 7. The distal end of the coil 3 (the distal end 76a of the distal end side coil 76) is fixed to the distal end of the core member 2 by a brazing metal 5. The distal end of the guide wire 70 formed of the brazing metal 5 constitutes a hemispherical distal end portion. The hemispherical distal end means that the distal end is formed in the shape of a substantially curved surface, inclusive of, for example, a hanging bell-like shape, a bullet-like shape and the like.

As has been described above, by providing the fixing member 74, the gap between the core member (fixing member) and the coil is reduced, so that the coil 3 can be fixed concentrically with the core member, and a distal end portion of the guide wire 70 undergoes generally uniform favorable deformations at the time of insertion into a living body.

Figure 15:
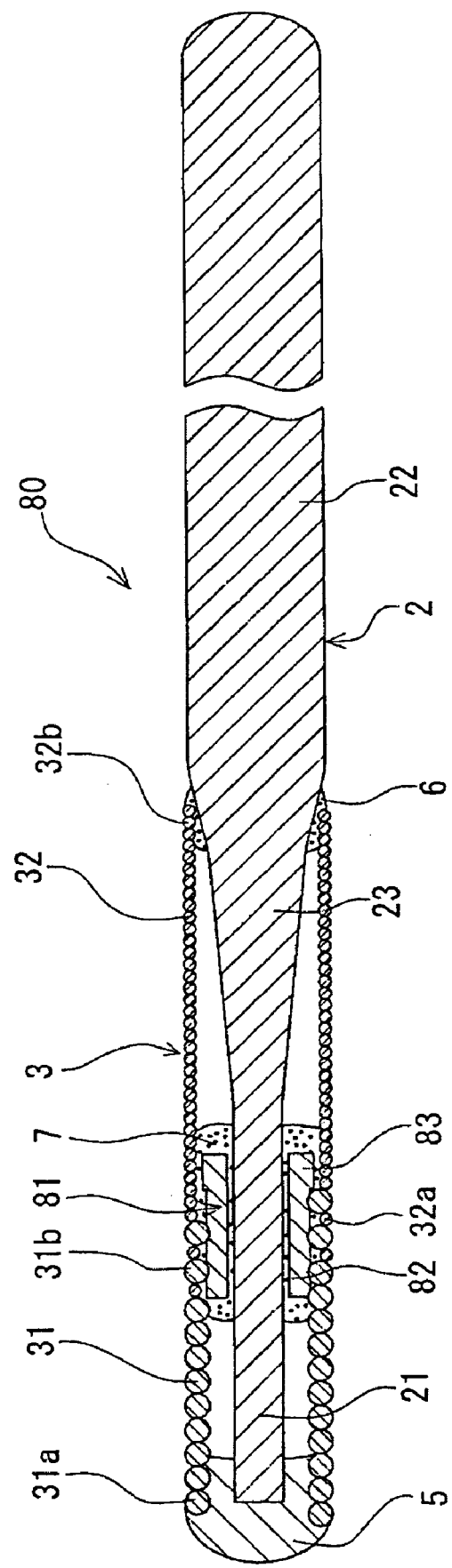
FIG. 15 is a partly omitted sectional view of a guide wire according to another embodiment.
Figure 16:
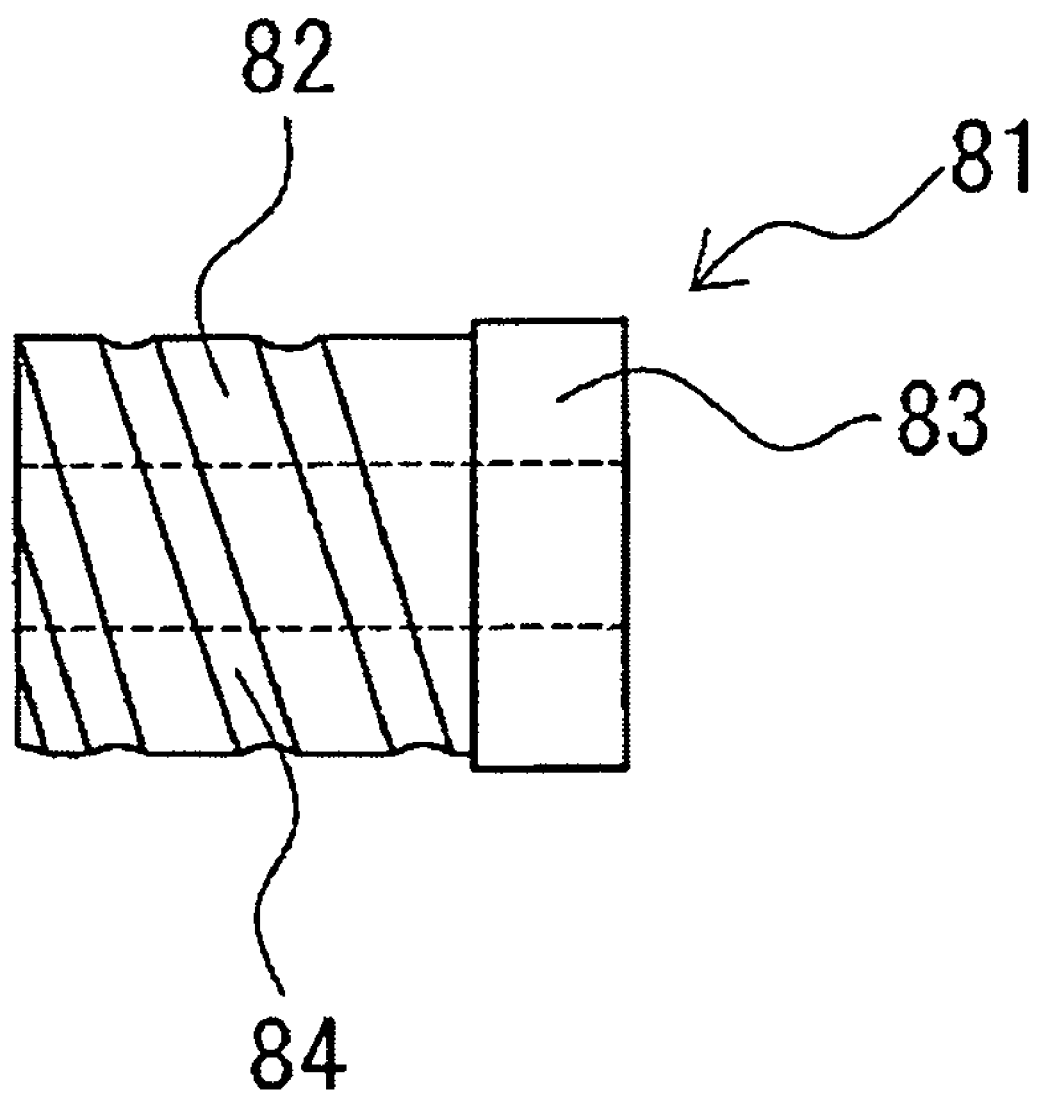
FIG. 16 is an appearance view of another example of a fixing member used in the guide wire.

FIG. 15 is a cross-sectional view of the guide wire according to another embodiment and FIG. 16 is a side view of another example of a tubular member used in the guide wire. The guide wire 80 shown in FIG. 15 is fundamentally the same as the above-described guide wire 1. The differences between the two lie primarily in the form of the coil fixing member. The following description will discuss primarily the differences and a description of other parts of the guide wire that are the same as those previously described will not be repeated.

In the guide wire 80 according to this embodiment, like in the guide wire 1 described above, the fixing member 81 is a tubular member as shown in FIGS. 15 and 16. As shown in FIG. 16, the fixing member 81 is provided at its outer surface with a spiral groove 84 corresponding to the shape of an inside portion of the coil. As shown in FIG. 15, an inside portion of a proximal end portion of a distal end side coil 31 is fitted in the groove 84 in the fixing member 81. In the guide wire 80 according to this embodiment, a proximal end portion 31b of the distal end side coil 31 and a distal end portion 32a of a proximal end side coil 32 overlap one another and are entangled with each other. In view of this, the groove 84 in the fixing member 81 has a relatively wide pitch.

As shown in FIG. 16, the fixing member 81 comprises a smaller diameter portion 82 corresponding in position to a proximal end portion of the distal end side coil 31, in the embodiment shown, the entangled portion of the distal end side coil 31 and the proximal end side coil 32, and a larger diameter portion 83 corresponding in position to a portion of the proximal end side coil 32 as shown in FIG. 15.

In addition, in the guide wire 80, the fixing member 81 is provided at the position of the entangled portion of the distal end side coil 31 and the proximal end side coil 32, in the same manner as in the above-described guide wire 1. The outside diameter of the smaller-diameter portion 82 of the fixing member 81 is slightly larger than the inside diameter of the distal end side coil 31. Also, the portion of the distal end side coil 31 to be located over the fixing member 81 enters into the above-mentioned groove 84. Therefore, the portion of the distal end side coil 31 to be located over the fixing member 81 maintains the same outside diameter as that of other portions. In addition, the outside diameter of the larger diameter portion 83 of the fixing member 81 is slightly smaller than the inside diameter of the proximal end side coil 32. The outside diameter of the larger diameter portion 83 of the fixing member 81 is preferably slightly greater than the inside diameter of the distal end side coil 31. This helps ensure that the rear end of the distal end side coil 31 abuts on an end portion of the larger diameter portion 83 of the fixing member 81 so that the distal end side coil 31 can be inhibited or prevented from moving. Furthermore, the operation of fixing the coil 3 to the core member 2 is facilitated.

The coil 3 is fixed to the coil fixing member 81 by a brazing metal 7 used as the adhesion material. Examples of the adhesion material include not only the abovementioned brazing metals (inclusive of solder) but also resin-made adhesives. The coil 3 is fixed to the coil fixing member 81 through the adhesion material. The adhesion material is disposed to fill the gap between the fixing member 81 and the core member 2.

By providing such a fixing member 81, the gap between the core member (fixing member) and the coil is reduced so that the coil 3 can be fixed concentrically with the core member 2, and, at the time of insertion into a living body, the distal end portion of the guide wire 80 undergoes generally uniform favorable deformations and a smooth torque transmissibility can be realized. In addition, the brazing metal is prevented from excessively flowing in the axial direction of the guide wire 80 at the time of fixation, so that the fixation portion of the coil 3 and the core member 2 can be made smaller in length.

The coil fixing member in the guide wire according to this embodiment is not limited to the above-described one. For example, the fixing member 4a shown in FIG. 5 may be adopted, in which the inside diameter of the lumen is provided with a groove or grooves 43 extending in the axial direction. A plurality of the grooves 43 are preferably provided, as illustrated. The provision of such grooves facilitates the flow of the brazing metal into the gap between the fixing member and the core member. The lumen at the portion of the large diameter portion 41 may constitute a portion 44 enlarged in diameter as compared with the other portions, as in the fixing member 4b shown in FIG. 6. By providing the enlarged diameter portion 44, the flow of the brazing metal into the gap between the fixing member and the core member is facilitated. In addition, the fixing member may be provided with slots 45 extending in the axial direction, as in the fixing member 4c shown in FIG. 7. A plurality of the slots 45 are preferably provided as described above and illustrated in FIG. 7. In the configuration shown in the figure, the slots 45 do not communicate with each other over the range from one end to the other end of the fixing member. As mentioned above, the slots facilitate the flow of the brazing metal into the gap between the fixing member and the core member and also facilitates the flow of the brazing metal into the gap between the fixing member and the coil.

In addition, the guide wire 80 according to this embodiment may also have the form of a distal end portion of the core member and the form of the lumen of the coil fixing member which are the same as those in the above-described guide wire 10.

Further, the coil in the guide wire of this embodiment is not limited to the above-described one. As in the guide wire 20 shown in FIG. 11, a coil 3 may be adopted in which a proximal end portion 31b of the distal end side coil 31 and a distal end portion 32a of the proximal end side coil 32 are not entangled with each other. In this case, the grooves 84 provided in the fixing member 81 could have a short pitch (equal to the pitch of the entire part of the distal end side coil) because the proximal end portion of the distal end side coil is not pushed wide open by the proximal end side coil. In other words, the pitch at the proximal end of the distal end side coil 31 is shorter than that shown in FIG. 15.

Furthermore, the coil in the guide wire according to this embodiment may be a single-element coil 3, as in the guide wire 30 shown in FIG. 12. In this case, as shown in FIG. 12, the coil 3 is entirely formed of the same elementary wire so that the entire part has substantially the same outside diameter and the same inside diameter. The coil fixing member in this case is a tubular member having substantially the same outside diameter as shown in FIG. 12. Then, the fixing member is provided in the entire outer surface thereof with a spiral groove of which the pitch is equal to the pitch of the coil.

The single-element coil includes not only one entirely formed of the same material, but also a coil in which the elementary wire on the distal end side is formed of a radiopaque material such as platinum, whereas the elementary wire on the proximal end side is formed of a material lower in radiopaque property than that on the distal end side, such as a stainless steel, and a proximal end portion of the distal end side elementary wire and a distal end portion of the proximal end side elementary wire are joined to each other so as to obtain an integral coil. In this case, the fixing member may be interposed between the core member and the coil as abovedescribed, at the joint portion of the elementary wires, or may be located on the distal end side and/or the proximal end side relative to the joint portion.

Further, the guide wire according to this embodiment may also have the form of the core member and the form of the coil which are the same as those in the guide wire 70 shown in FIG. 14.

Figure 17:
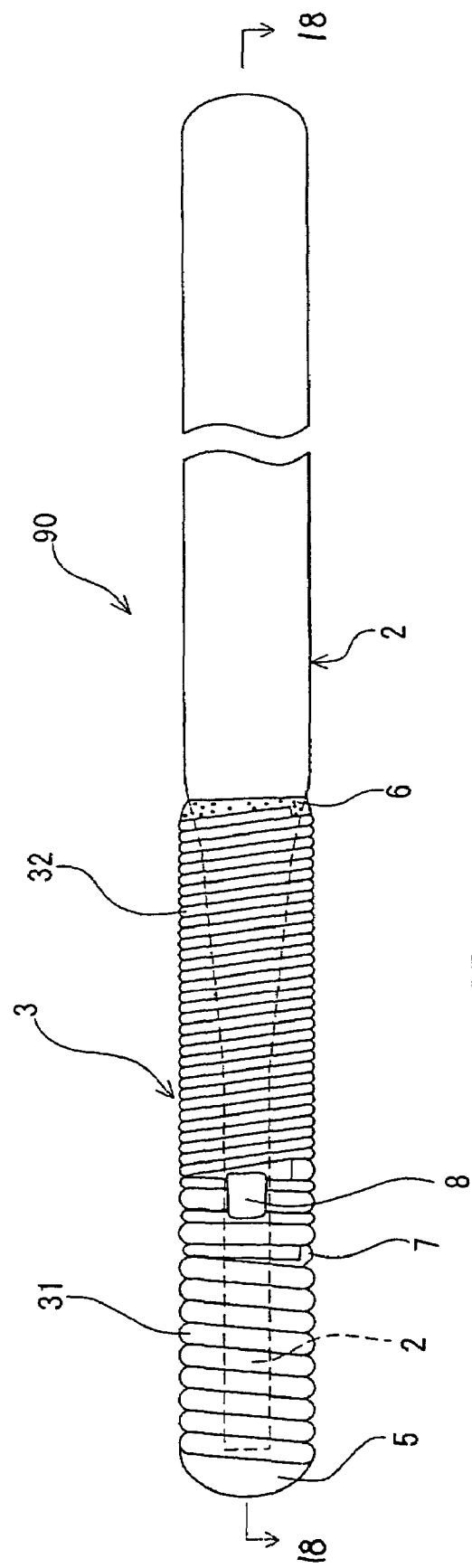
FIG. 17 is a partly omitted front view of a further embodiment of the guide wire.
Figure 18:
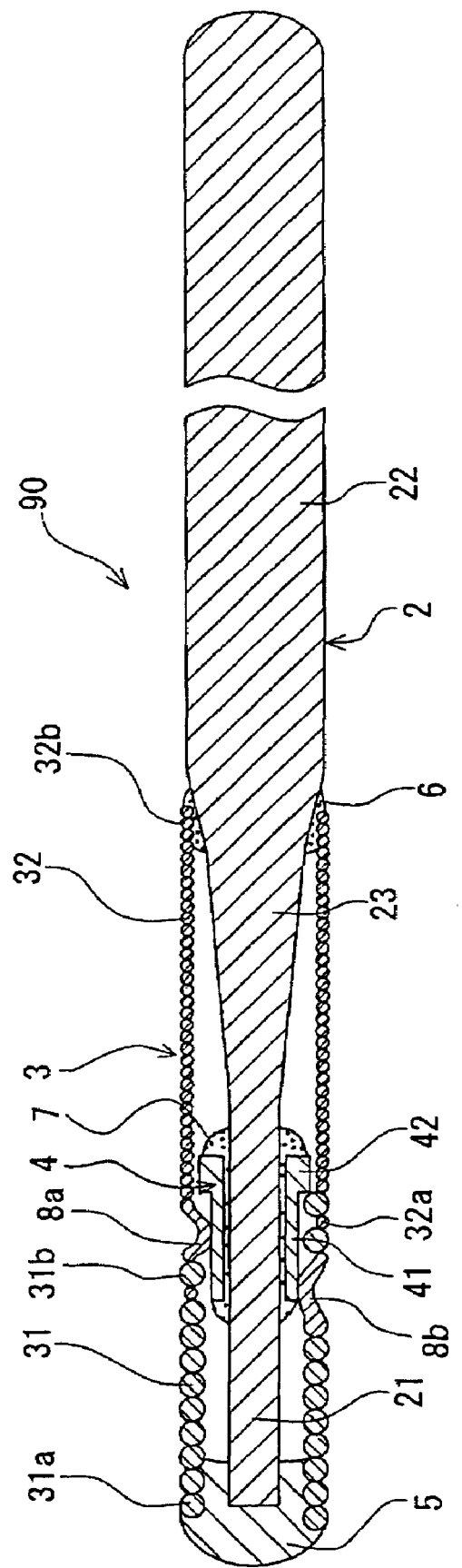
FIG. 18 is a sectional view along the section line 18-18 of the guide wire shown in FIG. 17.

FIG. 17 is a partly omitted front view of a further embodiment of the guide wire while FIG. 18 is a cross-sectional view of the guide wire along the section line 18-18 of the guide wire shown in FIG. 17. The guide wire 90 in this embodiment comprises a core member 2 and a coil 3 covering at least a distal end side portion of the core member 2. The guide wire 90 also comprises a coil fixing member 4 which is fixed to the distal end side portion of the core member 2 and which is adapted to fix the coil 3 concentrically with the core member 2 at least at a portion in the longitudinal direction of the coil 3, and the coil 3 is fixed to the coil fixing member 4 by welding.

In the guide wire 90 according to this embodiment, the coil 3 is fixed to the coil fixing member 4 by welding. The welding can be carried out by a known method such as laser welding, arc welding, and resistance welding. In the guide wire 90 in this embodiment, the fixation is carried out by laser welding, and the guide wire 90 comprises two fixing portions 8a, 8b. One 8a of the fixing portions is located at a central portion of the fixing member 4 or on the proximal end side of the central portion, and the other fixing portion 8b is located on the distal end side of the fixing member 4. Further, as shown in FIGS. 17 and 18, in the guide wire 90 according to this embodiment, the coil 3 is composed of a distal end side coil 31 and a proximal end side coil 32, with a proximal end portion 31b of the distal end side coil 31 and a distal end portion 32a of the proximal end side coil 32 overlapping one another and being entangled with each other. One 8a of the fixing portions fixes a proximal end portion of the entangled portion of the coils to the fixing member 4, and the other fixing portion 8b fixes a distal end portion of the entangled portion of the coils to the fixing member 4.

The fixing portions 8a, 8b are preferably portions at which the distal end side coil 31, the proximal end side coil 32 and at least the surface of the fixing member 41 have been melted and solidified with each other. The melted and solidified portions are portions at which the distal end side coil 31 and the proximal end side coil 32 have first been melted by irradiation with energy by the above-mentioned welding method, such as laser welding, and the surface of the fixing member 41 has also been melted, followed by solidification in the condition where the molten materials constituting the coils 31, 32 and the surface of the fixing member 41 have been mixed with each other. Since the melted and solidified portions are thus formed through mixing and solidification of the materials, the coils and the fixing member are firmly fixed at the fixing portions.

Examples of the material constituting the fixing member include metallic materials, e.g., noble metals such as gold and copper which are well compatible with the brazing metal (solder) such as silver solder; stainless steels, etc. The melting point of the material constituting the fixing member is preferably lower than the melting point of the material constituting the coils. In this case, since the fixing member is sufficiently larger than the coils in the area of the fixing portions, upon irradiation with energy such as laser, the coils and the surface of the fixing member are melted, but the fixing member is able to maintain its shape without being entirely melted. Other than the configuration in which the fixing member is formed of a material having a melting point lower than that of the material constituting the coils, it is possible that at least the surface of the fixing member is formed of a material having a melting point lower than that of the material constituting the coils. In the case where the coils have a two-layer structure composed of materials having different melting points (for example, the outer layer is formed of a stainless steel, which is relatively low in radiopaqueness, and the inner layer is formed of platinum, which is relatively high in radiopaqueness), the melting point of the coils can be calculated from the melting points and the cross section occupancy ratios of the individual materials.

In this embodiment, the two fixing portions 8a, 8b are spaced by a predetermined length from each other in the axial direction of the guide wire 90. Also, in this embodiment, the two fixing portions 8a, 8b are located at positions staggered by about 180 degrees from each other with respect to the center axis of the guide wire 90.

The locations of the fixing portions may be, for example, such that one 8a of the fixing portions is located at the distal end side coil and the fixing member on the distal end side relative to the entangled portion of the coils whereas the other fixing portion 8b is located at the proximal end side coil and the fixing member on the proximal end side relative to the entangled portion of the coils.

Incidentally, in the case of thus forming the fixing portions as spot portions, the number of fixing portions is not limited to the above-mentioned two as three or more may be provided. In addition, where three or more fixing portions are provided, the individual fixing portions are preferably provided at nearly equal angular intervals around the center axis of the guide wire. Furthermore, where three or more fixing portions are provided, the individual fixing portions are preferably provided at nearly equal intervals along the axial direction of the guide wire. It is also to be understood that the fixing portions are not limited to the above-mentioned spot-like portions but may be annular welds.

In all the guide wires according to the above-described embodiments, the coils may be fixed to the coil fixing member by welding. As the fixing portions formed by welding, the above-mentioned ones are preferred.

As shown in FIGS. 17 and 18, the guide wire 90 comprises the core member 2, and the coil 3 covering at least a distal end side portion of the core member 2. The coil 3 comprises the distal end side coil 31 and the proximal end side coil 32. As shown in FIG. 18, the coil fixing member 4 is adapted to fix a proximal end portion 31b of the distal end side coil 31 and a distal end portion 32a of the proximal end side coil 32 to the core member 2. The distal end of the coil 3, in this embodiment the distal end 31a of the distal end side coil 31, is fixed to a distal end portion of the core member 2. The proximal end of the coil 3, in this embodiment the proximal end 32b of the proximal end side coil 32, is fixed to a portion of the core member 2 on the proximal end side relative to the distal end of the core member 2 by a predetermined distance. Namely, in the guide wire 90 according to this embodiment, the distal end of the coil 3 is fixed to the distal end of the core member 2, while the proximal end of the coil 3 is fixed to the portion of the core member 2 on the proximal end side relative to the distal end of the core member 2 by a predetermined distance. The core member 2 constitutes a main body portion of the guide wire 90 extending from a proximal end portion of the coil 3.

The whole length of the guide wire 90 is preferably about 300 mm to 4500 mm, more preferably about 1000 mm to 2000 mm.

The core member 2 comprises a main body portion 22, a tapered portion 23, and a distal end portion 21, arranged in this order from the proximal end side. The main body portion 22 is an elongate portion having a substantially constant outside diameter and extending toward the distal end side from the proximal end of the core member 2, and the distal end portion 21 is smaller in diameter than the main body portion 22. In this embodiment, the distal end portion 21 extends toward the distal end side while having substantially the same diameter. The tapered portion 23 is formed between the distal end portion 22 and the main body portion 22.

The outside diameter of the guide wire 90 at the main body portion 22 is preferably 0.2 mm to 1.8 mm, more preferably about 0.3 mm to 1.6 mm. The outside diameter of the distal end portion 21 is 0.05 mm to 1.6 mm, and the length of the distal end portion 21 is 10 mm to 500 mm, preferably 20 mm to 300 mm. The distal end portion 21 may be more flexible on the distal end side; for example the distal end portion 21 may be gradually increased in flexibility approaching the distal end, by a heat treatment.

Examples of the material for constituting the core member 2 include various metallic materials such as superelastic alloys (e.g., Ni—Ti based alloy), stainless steels, and piano wire.

The whole length of the coil 3 is 10 mm to 500 mm, preferably 20 mm to 300 mm, and the outside diameter of the coil 3 is 0.2 mm to 1.8 mm, preferably 0.3 mm to 1.6 mm. The coil 3 covers the distal end portion 21 and the tapered portion 23 of the core member 2. The distal end of the coil 3 is fixed to the distal end of the core member 2, and the proximal end of the coil 3 is attached to a proximal end portion of the tapered portion 23 by a brazing metal 6 or the like.

In this embodiment, the coil 3 is composed of the distal end side coil 31 and the proximal end side coil 32 as shown in FIGS. 17 and 18. Further, a proximal end portion 31b of the distal end side coil 31 and a distal end portion 32a of the proximal end side coil 32 axially overlap one another and are entangled with each other. The entanglement of the two coils 31, 32 helps prevent them from being spaced away from each other. The distance over which the two coils 31, 32 are entangled with each other is preferably about 0.1 mm to 2 mm.

In addition, the distal end side coil 31 and the proximal end side coil 32 preferably have different physical properties. The physical properties of the two coils 31, 32 can be variously selected according to the purpose of the guide wire. For example, the distal end side coil may be more flexible than the proximal end side coil (the flexibility of the coil can be changed, for example, by winding the elementary wire of the coil with or without a gap between the adjacent turns of the elementary wire, by changing the diameter of the elementary wire of the coil, or by changing the material of the coil). The distal end side coil may be higher in radiopaque property than the proximal end side coil. In this embodiment, the gap between adjacent turns of the elementary wire of the distal end side coil 31 is larger than the gap between adjacent turns of the elementary wire of the proximal side coil 32. Further, the diameter of the elementary wire of the distal end side coil 31 is larger than the diameter of the elementary wire of the proximal end side coil 32. The distal end side coil 31 and the proximal end side coil 32 are nearly equal in outside diameter. The length of the distal end side coil 31 is preferably 3 mm to 60 mm, and the length of the proximal end side coil 32 is preferably 10 mm to 40 mm. In addition, the distal end side coil 31 is smaller in inside diameter than the proximal end side coil 32.

Examples of the material usable for forming the coils include superelastic alloys (e.g., Ni—Ti based alloy), stainless steels, and noble metals such as gold and platinum. The distal end side coil 31 and the proximal end side coil 32 may be formed of the same material or may be formed of different materials. Where different materials are used for forming the coils 31, 32, it is possible, for example, to use a noble metal such as gold and platinum for the distal end side coil 31 and a stainless steel for the proximal end side coil 32, or to use a superelastic alloy for the distal end side coil 31 and a stainless steel for the proximal end side coil 32.

The distal end of the coil 3 is fixed to the distal end of the core member 2 by a brazing metal 5. The distal end of the guide wire 90 formed of the brazing metal 5 is a hemispherical distal end portion. The hemispherical distal end means that the distal end is in the shape of a substantially curved surface, inclusive of, for example, a hanging bell-like shape, a bullet-like shape and the like.

The coil fixing member 4 is fixed to a distal end portion of the core member 2. The fixation of the fixing member 4 to the core member 2 may be carried out by any method such as fitting and brazing (soldering). The fixing member 4 is for fixing the coil 3 concentrically with the core member 2 at least at a portion in the longitudinal direction of the coil 3. The length of the fixing member 4 is preferably about 0.2 mm to 1.0 mm.

In this embodiment, the position of the fixing member 4 in the coil 3 is located on the distal end side relative to a middle portion in the longitudinal direction of the coil 3. However, the position may be located nearly at the middle portion in the longitudinal direction of the coil 3, or on the proximal end side relative to the middle portion in the longitudinal direction of the coil 3. The position of the fixing member 4 in the coil 3 is spaced by a predetermined distance from the distal end or the proximal end of the coil 3. In addition, a plurality of fixing members 4 may be provided. For example, the fixing members 4 may be located at positions spaced by predetermined distances to the distal end side and the proximal end side from the portion where the distal end side coil 31 and the proximal end side coil 32 are joined to each other, and fixation between the distal end side coil 31 and the distal end side fixing member and fixation between the proximal end side coil 32 and the proximal end side fixing member may be performed through an adhesion material such as a brazing metal.

In the guide wire 90 according to this embodiment, the fixing member 4 is a tubular member, as shown in FIG. 18. Further, the fixing member 4 comprises a smaller diameter portion 41 corresponding in position to a proximal end portion of the distal end side coil 31, in the embodiment shown the entangled portion of the distal end side coil 31 and the proximal end side coil 32, and a larger diameter portion 42 corresponding in position to the proximal end side coil 32 as illustrated in FIG. 18. In the guide wire 90, the fixing member 4 is provided at the position of the entangled portion of the distal end side coil 31 and the proximal end side coil 32. The outside diameter of the smaller diameter portion 41 of the fixing member 4 is slightly smaller than the inside diameter of the distal end side coil 31. The outside diameter of the larger diameter portion 42 of the fixing member 4 is slightly smaller than the inside diameter of the proximal end side coil 32. In addition, the outside diameter of the larger diameter portion 42 of the fixing member 4 is preferably slightly larger than the inside diameter of the distal end side coil 31. This helps ensure that, as shown in FIG. 18, the rear end of the distal end side coil 31 abuts on an end portion of the large diameter portion 42 of the fixing member 4 so that the distal end side coil 31 can be inhibited or prevented from moving. Further, the operation of fixing the coil 3 to the core member 2 is facilitated. In the fixing member 4 used in this embodiment, the axial length of the larger diameter portion 42 is smaller than the axial length of the smaller diameter portion 41.

In the guide wire 90 according to this embodiment, the coil 3 is fixed to the coil fixing member 4 by welding. The welding may be carried out by a known method such as laser welding, arc welding, and resistance welding. Laser welding is preferred, since it is possible to minutely regulate the spot diameter at the irradiation portions, and to regulate the irradiation intensity and time according to the materials at the irradiation portions. For example, the irradiation intensity for the coil formed of a material with a higher melting point can be set higher than the irradiation intensity for the coil formed of a material with a lower melting point.

By providing such a fixing member 4, the gap between the core member (fixing member) and the coil is reduced so that the coil 3 can be fixed concentrically with the core member 2, and, at the time of insertion into a living body, a distal end portion of the guide wire 90 undergoes generally uniform favorable deformations and a smooth torque transmissibility can be realized. Additionally, the brazing metal is prevented from excessively flowing in the axial direction of the guide wire 90, and the length of the fixing portion between the coil 3 and the core member 2 can be made smaller.

In the guide wire 90 according to this embodiment, the coil fixing member is not limited to the above-described one. For example, the fixing member 4a shown in FIG. 5 may be adopted in which the inside wall of the lumen is provided with a groove or grooves 43 extending in the axial direction. A plurality of grooves 43 are preferably provided in such a case, as shown in FIG. 5. These grooves help facilitate the flow of the brazing metal into the gap between the fixing member and the core member. Also, the fixing member 4b shown in FIG. 6 may be used in which the lumen at the portion of the larger diameter portion 41 is a portion 44 enlarged in diameter as compared with the other portions. With the enlarged diameter portion 44, the flow of the brazing metal into the gap between the fixing member and the core member is facilitated. In addition, the fixing member 4c shown in FIG. 7 may be used in which the fixing member is provided with a slot or slots 45 extending in the axial direction. A plurality of slots 45 are preferably provided in such a case as shown. In the illustrated version of the fixing member 4c, the slots 45 do not communicate with each other over the range from one end to the other end of the fixing member. The provision of such slots facilitates the flow of the brazing metal into the gap between the fixing member and the core member and also the flow of the brazing metal into the gap between the fixing member and the coil.

In addition, the guide wire 90 in this embodiment may also comprise the form of a distal end portion of the core member and the form of the lumen of the coil fixing member which are the same as those in the above-described guide wire 10. The coil in the guide wire according to this embodiment can be a single-element coil 3 such as used in the guide wire 30 shown in FIG. 12.

The guide wire 90 in this embodiment may also have the form of the core member and the form of the coil which are the same as those in the guide wire 70 shown in FIG. 14. Further, in the guide wire 90 according to this embodiment, the outer surface of the fixing member may be provided with a spiral groove corresponding to the shape of an inside portion of the coil, like those shown in FIGS. 15 and 16, and the inside portion of a proximal end portion of the distal end side coil 31 may enter into the groove in the fixing member as shown in FIG. 15.

In all of the above embodiments, the entire outside surface of the guide wire or the outside surface of a desired portion of the guide wire may be coated with a lubricity imparting agent for lowering the frictional resistance between the outside surface and the tubular inside surface of a catheter or the like.

As the lubricity imparting agent, water-soluble polymeric materials or derivatives thereof may be preferably used. Examples of the lubricity imparting agent include poly (2-hydroxyethyl methacrylate) polyhydroxyethyl acrylate, cellulose-based polymeric materials (e.g., hydroxypropyl cellulose, hydroxyethyl cellulose), maleic anhydride-based polymeric materials (e.g., methyl vinyl ether-maleic anhydride copolymer), acrylamide-based polymeric materials (e.g., polyacrylamide), polyethylene oxide-based polymeric materials (e.g., polyethylene oxide, polyethylene glycol), polyvinyl alcohol, polyacrylic acid-based polymeric materials (e.g., sodium polyacrylate), phthalic acid-based polymeric materials (e.g., polyhydroxyethyl phthalate), water-soluble polyesters (e.g., polydimethylol propionate), ketone-aldehyde resins (e.g., methyl isopropyl ketone formaldehyde), polyvinyl pyrrolidone, polyethyleneimine, polystyrene sulfonate, and water-soluble nylons.

Figure 19:
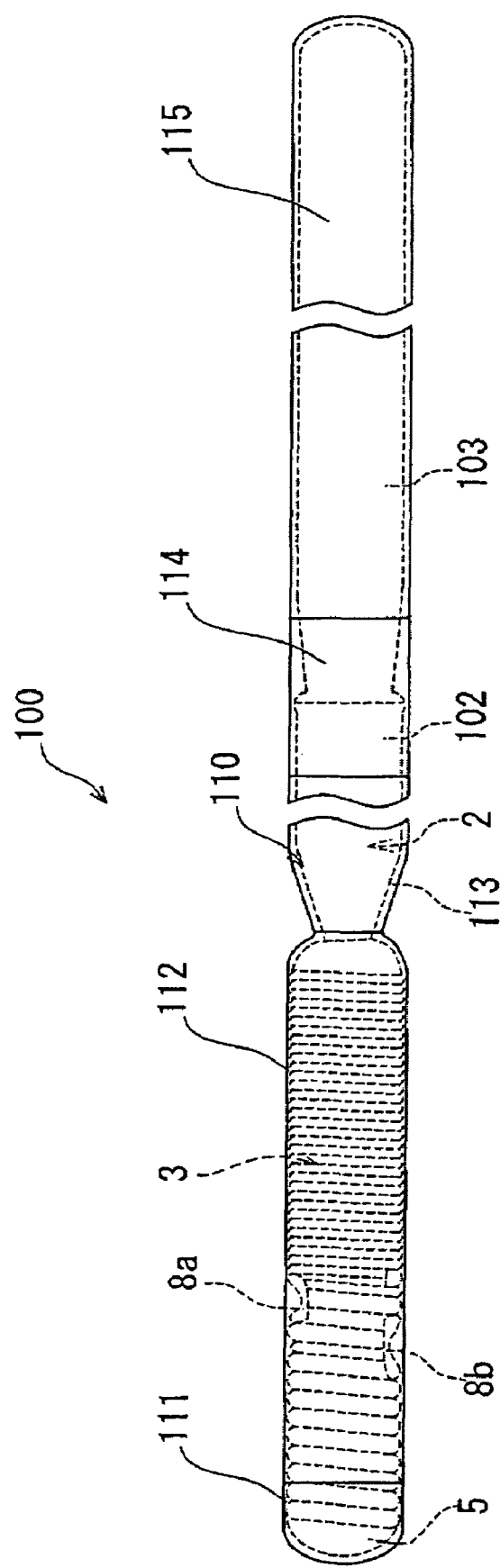
FIG. 19 is a partly omitted front view of yet another embodiment of the guide wire.
Figure 20:
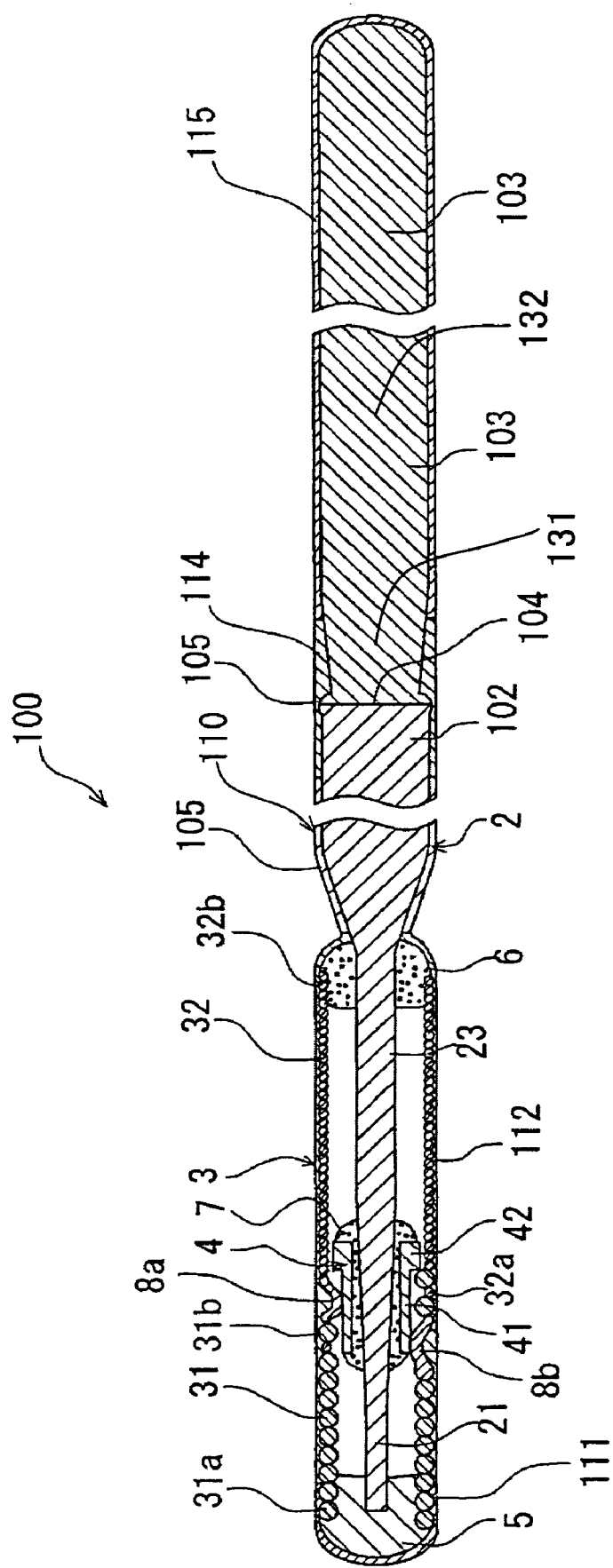
FIG. 20 is a partly omitted sectional view of the guide wire shown in FIG. 19.
Figure 21:
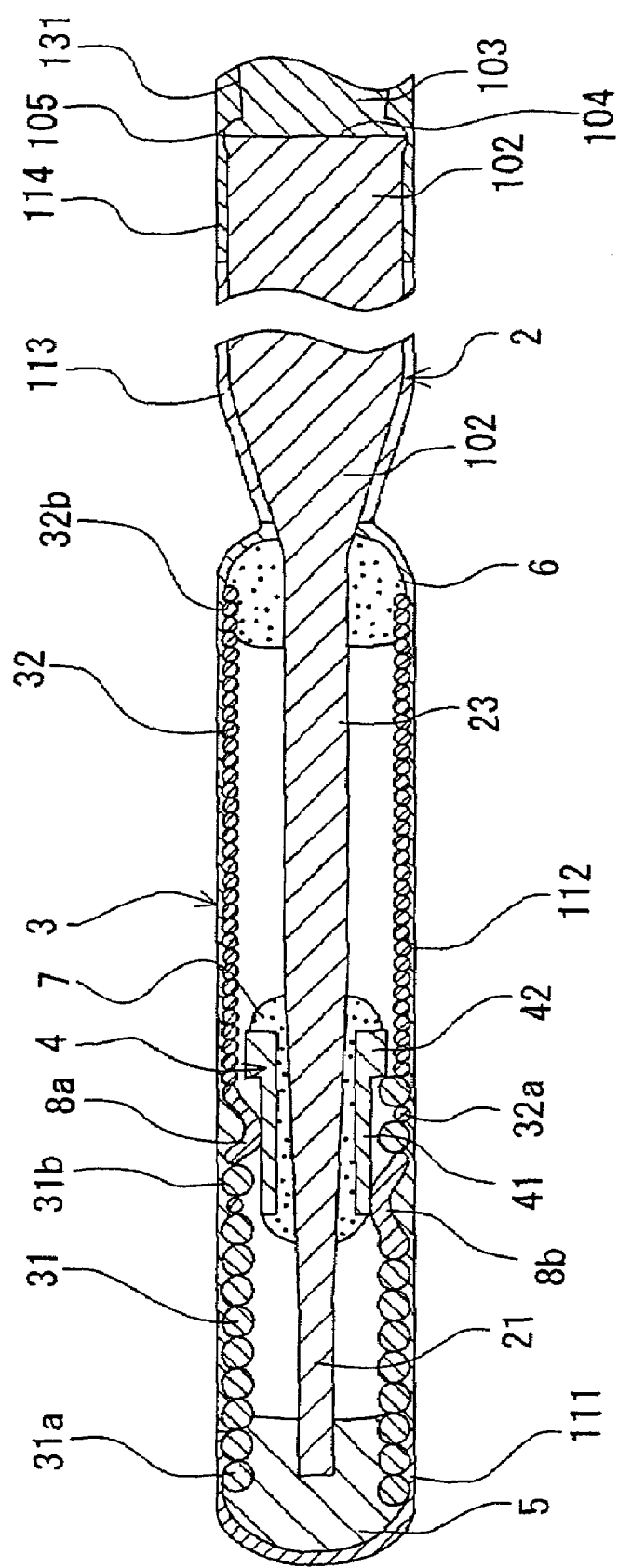
FIG. 21 is an enlarged sectional view of a distal end portion of the guide wire shown in FIG. 19.

Further, in all the guide wires according to the above-described embodiments, the core member 2 may be in the form of the guide wire 100 shown in FIGS. 19-21. Further, in all the guide wires according to the above embodiments, the guide wire may be the guide wire 100 shown in FIGS. 19-21 which comprises a surface coating layer.

The fundamental configuration of the guide wire shown in FIGS. 19-21 is primarily the same as that of the guide wire 90 according to the above embodiment, the fundamental configuration may be that of any one of the guide wires according to the above embodiments. Also, the fixing member may be any one of those shown in FIGS. 5-9 and 16.

In the guide wire 100, the core member 2 is composed of a distal end side core member 102 and a proximal end side core member 103. The proximal end of the distal end side core member 102 is fixed to the distal end of the proximal end side core member 103.

The distal end side core member 102 is an elastic wire member. The length of the distal end side core member 102 is not particularly limited, but is preferably 20 mm to 100 mm. In the guide wire 100 according to this embodiment, the distal end side core member 102 has a constant outside diameter over a predetermined length from the proximal end thereof, and, from an intermediate point, the outside diameter is gradually decreased toward the distal end.

The material constituting the distal end side core member 102 is not particularly limited. For example, various metallic materials such as stainless steels can be used as the material. Among the various metallic materials, particularly preferred include alloys showing pseudo-elasticity (inclusive of superelastic alloys), and more preferred are superelastic alloys. Superelastic alloys are comparatively flexible, have a excellent resiliency, and are relatively insusceptible to sustained or recurring bending. With the distal end side core member 102 formed of a superelastic alloy, the guide wire 100 is provided with sufficient flexibility and resiliency against bending at a distal end side portion thereof. Therefore, the guide wire 100 is enhanced in traceability to bent blood vessels that are curved in a relatively complicated manner, and can acquire an excellent operationality. Further, even when the distal end side core member 102 is subjected to repeated curving or bending deformations, the distal end side core member 102 is not imparted with a sustained or recurring bending because of its resiliency. Therefore, the operationality can be prevented from being lowered due to a sustained or recurring bending imparted to the distal end side core member 102 in the use of the guide wire 100.

The pseudo-elastic alloys include those alloys of any shape of tensile stress-strain curves, including those alloys for which transformation points such as As, Af, Ms, and Mf can be conspicuously measured or cannot be measured, and include all the alloys which are largely deformed (strained) under stress and which substantially restore to their original shape thereof upon removal of the stress.

Preferable compositions of the superelastic alloys include Ni—Ti based alloys such as Ni—Ti alloys containing 49 to 52 at % (atom %) of Ni, Cu—Zn alloys containing 38.5 to 41.5 wt % Zn, Cu—Zn—X alloys containing 1 to 10 wt % of X (X is at least one selected from the group consisting of Be, Si, Sn, Al, and Ga), and Ni—Al alloys containing 36 to 38 at % (atom %) of Al. Among these, particularly preferred are the Ni—Ti based alloys.

The distal end of the proximal end side core member 103 is coupled (connected) to the proximal end of the distal end side core member 102 by welding. The proximal end side core member 103 is an elastic wire member. The length of the proximal end side core member 103 is not particularly limited, but is preferably about 20 mm to 4800 mm.

The proximal end side core member 103 is formed of a material which is higher in elastic modulus (Young's modulus (modulus of longitudinal elasticity), shear modulus (modulus of transverse elasticity), bulk modulus) than the material constituting the distal end side core member 102. This helps ensure that the proximal end side core member 103 can have an appropriate rigidity (flexural rigidity, torsional rigidity), and the guide wire 100 is enhanced in rigidity and in pushability and torque transmissibility, leading to better operationality for insertion.

The material constituting the proximal end side core member is not particularly limited. Examples of the material which can be used include various metallic materials such as stainless steels (for example, all SUS series such as SUS304, SUS303, SUS316, SUS316L, SUS316J1, SUS316J1L, SUS405, SUS430, SUS434, SUS444, SUS429, SUS430F, and SUS302), piano wire, cobalt-based alloys, and pseudo-elastic alloys.

Among others, the cobalt-based alloys show a high elastic modulus when formed into a wire, and have an appropriate elastic limit. Therefore, a proximal end side core member 103 formed of a cobalt-based alloy has been found to have a particularly excellent torque transmissibility, and is for the most part extremely insusceptible to such problems as buckling. The cobalt-based alloys may have any composition, as long as it contains Co as a constituent element. Among the cobalt-based alloys, however, preferred ones are those which contain Co as a main constituent (Co-based alloys: alloys in which the content, by weight, of Co is the highest of the contents of constituent elements), and more preferred are Co—Ni—Cr based alloys. When an alloy of such a composition is used as the material of the proximal end side core member 103, the above-mentioned effects are obtained more remarkably. In addition, an alloy of such a composition is high in elastic modulus, and can be cold worked even when it is provided with a high elastic limit. Additionally, the high elastic limit makes it possible to reduce the diameter of the wire material while sufficiently preventing the generation of buckling, and to form a proximal end side core member 103 which has sufficient flexibility and rigidity for insertion to a predetermined site.

Preferred examples of the Co—Ni—Cr based alloys include alloys containing 28 to 50 wt % of Co, 10 to 30 wt % of Ni, and 10 to 30 wt % of Cr, the balance being Fe, and alloys obtained by substituting part of the component elements of the just-mentioned alloys by other elements (substituent elements). The content of the substituent elements displays an effect intrinsic of the kinds of the substituent elements. For example, when at least one selected from the group consisting of Ti, Nb, Ta, Be, and Mo is used as the substituent element, it is possible, for example, to further enhance the strength of the proximal end side core member 103. When elements other than Co, Ni, and Cr are contained, the total content of the substituent elements is preferably not more than 30 wt %.

In addition, part of Co, Ni, and Cr may be substituted by other element(s). For example, part of Ni may be substituted with Mn. This makes it possible, for example, to further improve the workability of the alloy. Besides, part of Cr may be substituted with Mo and/or W. This makes it possible, for example, to further improve the elastic limit of the alloy. Among the Co—Ni—Cr based alloys, preferred ones are those containing Mo, namely, Co—Ni—Cr—Mo based alloys.

Specific examples of the composition of Co—Ni—Cr based alloy include [1] 40 wt % Co-22 wt % Ni-25 wt % Cr-2 wt % Mn-0.17 wt % C-0.03 wt % Be-the balance Fe; [2] 40 wt % Co-15 wt % Ni-20 wt % Cr-2 wt % Mn-7 wt % Mo-0.15 wt % C-0.03 wt % Be-the balance Fe; [3] 42 wt % Co-13 wt % Ni-20 wt % Cr-1.6 wt % Mn-2 wt % Mo-2.8 wt % W-0.2 wt % C-0.04 wt % Be-the balance Fe; [4] 45 wt % Co-21 wt % Ni-18 wt % Cr-1 wt % Mn-4 wt % Mo-1 wt % Ti-0.02 wt % C-0.3 wt % Be-the balance Fe; and [5] 34 wt % Co-21 wt % Ni-14 wt % Cr-0.5 wt % Mn-6 wt % Mo-2.5 wt % Nb-0.5 wt % Ta-the balance Fe. The Co—Ni—Cr based alloys in the present invention include these alloys.

In addition, when a stainless steel is used as the material constituting the proximal end side core member 103, the guide wire 100 has further excellent pushability and torque transmissibility.

The distal end side core member 102 and the proximal end side core member 103 are preferably formed of different alloys. Also, it is preferable that the distal end side core member 102 is formed of a material which is lower in elastic modulus than the material constituting the proximal end side core member 103. This helps ensure that the guide wire 100 has excellent flexibility at a distal end side portion thereof, and the proximal end side portion possesses good rigidity (flexural rigidity, torsional rigidity). As a result, the guide wire 100 acquires relatively excellent pushability and torque transmissibility, thereby securing favorable operationality, and favorable flexibility and restoring properties are obtained on the distal end side, whereby the trackability along blood vessels and safety are enhanced.

In addition, as a specific combination of the distal end side core member 102 and the proximal end side core member 103, a particularly preferred combination is one in which the distal end side core member 102 is formed of a superelastic alloy and the proximal end side core member 103 is formed of a Co—Ni—Cr based alloy or a stainless steel. This helps ensure that the above-mentioned effects are displayed more conspicuously.

In the guide wire 100, the proximal end side core member 103 has a gradually decreased outside diameter portion (tapered diameter decrease portion) 131 in the vicinity of the distal end thereof. Specifically, the proximal end side core member 103 comprises a first portion 131 provided in the vicinity of the distal end thereof, and a second portion 132 provided on the proximal end side relative to the first portion 131 and higher in rigidity than the first portion 131. This contributes to producing an effect such that elasticity varies smoothly between the distal end side core member 102 and the proximal end side core member 103.

In the guide wire 100, a weld portion 104 between the distal end side core member 102 and the proximal end side core member 103 is provided with a projected portion 105 projected radially outwardly in the outer circumferential direction. By providing this projected portion 105, the area of joint between the distal end side core member 102 and the proximal end side core member 103 is enlarged, leading to a particularly high joint strength. As a result, in the guide wire 100, torsional torque and a pushing-in force are securely transmitted from the proximal end side core member 103 to the distal end side core member 102.

The height of the projected portion 105 is not particularly limited, and is preferably 0.001 mm to 0.3 mm, more preferably 0.005 mm to 0.05 mm.

In all the guide wires 1, 10, 20, 30, 40, 70, 80, and 90 according to the above-described embodiments, the core member may be the one shown in relation to the above guide wire 100.

In the guide wire 100, the outside surface of the guide wire can be coated with a coating layer 110. The coating layer 110 covers the gradually decreased outside diameter portion 131 and the projected portion 105 of the proximal end side core member 103 in such a manner as to provide a substantially uniform outside diameter. It is to be noted that a variation in the outside diameter which does not produce trouble in use is included in the expression "substantially uniform outside diameter".

In the guide wire 100 according to this embodiment, the coating layer 110 can comprise a plurality of coating portions formed of different coating materials. In this embodiment, the coating-layer 110 comprises a distal end coating portion 111 for coating a distal end portion of the guide wire inclusive of a distal end portion of the coil, a coil coating portion 112 for coating the coil portion, a proximal end portion coating portion 113 of the distal end side core member 102 for coating a proximal end portion of the distal end side core member 102, a joint portion coating portion 114 for coating the joint portion between the distal end side core member and the proximal end side core member, and a proximal end side core member coating portion 115 for coating the proximal end side core member.

The distal end coating portion 111 coats the outside surface of the portion of the brazing metal 5, which fixes the distal end of the distal end side core member 102 and the distal end of the coil 3 to each other, and the outside surface of a distal end portion of the coil 3.

The joint portion coating portion 114 coats the outside surfaces of a proximal end portion of the distal end side core member 102, the joint portion 104 between the proximal end of the distal end side core member 102 and the proximal end side core member 103, the projected portion 105 formed at the joint portion 104, and the tapered portion 131 of the proximal end side core member 103.

The distal end coating portion 111 and the joint portion coating portion 114 are preferably formed of a material having such a good formability as to form a substantially uniform outside diameter. Further, a material capable of reducing friction is preferably used. This makes it possible to provide the guide wire at this portion with a substantially uniform outside diameter, and to reduce the frictional resistance (sliding resistance) between the guide wire and the inside wall of a catheter in which the guide wire is inserted.

Examples of such a material having favorable formability and being not high in frictional resistance include silicone resins such as silicone rubbers, etc., polyurethane, other various elastomers (e.g., polyamide-based, polyester-based or other thermoplastic elastomers), polyolefins such as polyethylene, polypropylene, etc., polyvinyl chloride, polyesters (PET, PBT, etc.), polyamides, polyimides, polyurethane, polystyrene, polycarbonate, fluororesins (PTFE, ETTE, etc.), and composite materials of these. Among these materials, particularly preferred materials are silicone resins inclusive of silicone rubbers.

When the coating portion is constituted of a silicone resin (or a composite material containing the same), it is possible to form a coating portion in a secure and firm close contacting state, without heating, at the time of coating the portion relevant to the coating portion. Specifically, where the coating portion is constituted of a silicone resin (or a composite material containing the same), a reaction-curable material or the like can be used, so that the coating portion can be formed at room temperature.

In addition, the proximal end portion coating portion 113 and the proximal end side core member coating portion 115 for coating the proximal end side core member are preferably composed of a material capable of reducing friction. This reduces the frictional resistance (sliding resistance) between a distal end portion of the guide wire and the inside wall of the catheter used therewith, whereby slidability is enhanced and the operationality of the guide wire in the catheter is enhanced.

Examples of such a material capable of reducing friction include fluororesins such as PTFE, ETFE, etc., polyolefins such as polyethylene, polypropylene, etc., polyvinyl chloride, polyesters (PET, PBT, etc.), polyamides, polyimides, polyurethane, polystyrene, polycarbonate and composite materials of these. Among these materials, particularly preferred materials are fluororesins.

In addition, the coil coating portion 112 preferably displays lubricity through wetting (water absorption). As the material displaying lubricity through wetting (water absorption), many hydrophilic materials can be used. Specific examples of the hydrophilic materials include cellulose-based polymeric materials, polyethylene oxide-based polymeric materials, maleic anhydride-based polymeric materials (e.g., maleic anhydride copolymers such as methyl vinyl ether-maleic anhydride copolymer), acrylamide-based polymeric materials (e.g., block copolymer of polyacrylamide and polyglycidyl methacrylate-dimethyl acrylamide (PGMA-DMAA)), water-soluble nylons, polyvinyl alcohol, and polyvinyl pyrrolidone.

By providing such coating portions, the frictional resistance (sliding resistance) between the guide wire 100 and the inside wall of a catheter used with the guide wire 100 is extremely reduced. This enhances the slidability of the guide wire, thereby enhancing the operationality of the guide wire 100 in the catheter.

The thickness of each of the coating portions is not particularly limited. Ordinarily, the thickness (average) is preferably about 1 µm to 20 µm, more preferably about 2 µm to 10 µm.

A preferred example of the combination of the' materials for forming the coating portions in the coating layer 110 is such that the joint portion coating portion 114 is formed of a silicone resin (or a composite material containing the same), whereas the proximal end portion coating portion 113 and the proximal end side core member coating portion 115 are each formed of a fluororesin (or a composite material containing the same).

This makes it possible for the coating layer 110 to have both the merits of the silicone resin and the merits of the fluororesin. Specifically, when the above-mentioned combination is used as the materials constituting the coating portions in the coating layer 110, the guide wire 100 as a whole can have a sufficient slidability and display an excellent operationality, while the joint strength between the distal end side core member and the proximal end side core member at the weld portion is maintained.

In addition, where the above-mentioned combination is used for the material constituting the joint portion coating portion 114, it is preferable not to heat the core member 2 at the time of forming the coating portion 114 and to heat the core member 2 at the time of forming the proximal end portion coating portion 113 and the proximal end side core member coating portion 115. This enhances remarkably the close contact property between the proximal end portion coating portion 113 and the proximal end side core member coating portion 115 and the core member 2, and the close contact property between the proximal end side coating layer 7 and the wire main body.

In all of the guide wires 1, 10, 20, 30, 40, 80, 90 according to the above-described embodiments except for the guide wire 70, the coating portion 110 is preferably provided in the same manner as in the guide wire 100. The configuration of the coating portion 110 is preferably as above-described.

While it is preferable to provide the distal end coating portion 111 having the above-described configuration, the distal end coating portion 111 may be integral with the coil coating portion 112. Also, while it is preferable to provide the proximal end portion coating portion 113 configured as above-described, the proximal end portion coating portion 113 may be integral with the coil coating portion 112 or with the joint portion coating portion 114.

The principles, preferred embodiments and modes of operation of the present invention have been described in the foregoing specification. However, the invention which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. A guide wire comprising:
   a core member comprising a distal end side portion and a proximal end side portion, the distal end side portion being located on a distal side of the proximal end side portion;
   a coil covering at least the distal end side portion of said core member;

a coil fixing member constituting a metallic member that is separate from said core member and said coil, said coil fixing member being not a brazed joint and being connected to said distal end side portion of said core member at a point where the coil fixing member directly overlies the core member to connect said coil concentrically with said core member at least at a portion in the longitudinal direction of said coil, and said coil being fixed to said coil fixing member by an adhesion material, wherein said coil comprises a distal end side coil and a proximal end side coil, and said coil fixing member connects a proximal end portion of said distal end side coil and a distalmost end portion of said proximal end side coil to said core member, wherein said distal end side coil and said proximal end side coil have different inside diameters, and wherein an outside diameter of said distal end side portion of said core member decreases toward a distal end of said guide wire, said coil fixing member is a tubular body having a lumen, and an inside diameter of said lumen of said coil fixing member decreases toward the distal end following a shape of said distal end side portion.

2. A guide wire as set forth in claim 1, wherein said distal end side coil and said proximal end side coil have different physical properties.

3. A guide wire as set forth in claim 1, wherein said proximal end portion of said distal end side coil and said distalmost end portion of said proximal end side coil are entangled with each other.

4. A guide wire as set forth in claim 1, wherein said coil fixing member has a smaller diameter portion and a larger diameter portion, with the smaller diameter portion of the coil fixing member being axially positioned within the distal end side coil and the larger diameter portion of the coil fixing member being axially positioned within the proximal end side coil.

5. A guide wire as set forth in claim 1, wherein a distal end of said coil is fixed to a distal end of said core member, a proximal end of said coil is fixed to a portion of said core member which is spaced a predetermined distance on a proximal end side of the distal end of said core member, and said core member constitutes a main body portion of said guide wire, said main body portion extending from a proximal end portion of said coil.

6. A guide wire as set forth in claim 1, wherein said coil is fixed to said coil fixing member by welding.

7. A guide wire as set forth in claim 6, wherein a melting point of the material forming said coil fixing member is lower than a melting point of the material forming said coil.

8. A guide wire as set forth in claim 1, wherein said coil fixing member is spaced a predetermined distance from a distal end or a proximal end of said coil.

9. A guide wire comprising:
a core member having a distal end side portion;
a coil covering at least said distal end side portion of said core member and comprising a distal end side coil and a proximal end side coil;
said distal end side coil and said proximal end side coil possessing different inside diameters;
a coil fixing member directly connected to at least a portion of said distal end side portion of said core member to fix said coil with said core member at least at a portion in a longitudinal direction of said coil;
said coil fixing member comprising a smaller diameter portion and a larger diameter portion;
the smaller diameter portion of the coil fixing member being located to axially correspond in position to one of the distal end side coil and the proximal end side coil having a smaller inside diameter;
the larger diameter portion of the coil fixing member being located to axially correspond in position to one of the distal end side coil and the proximal end side coil having a larger inside diameter; and
an outside diameter of said larger diameter portion of said coil fixing member being larger than the inside diameter of the one of the distal end side coil and the proximal end side coil possessing said smaller inside diameter, wherein an outside diameter of said distal end side portion of said core member decreases toward a distal end of said guide wire, said coil fixing member is a tubular body having a lumen, and an inside diameter of said lumen of said coil fixing member decreases toward the distal end following a shape of said distal end side portion.

10. A guide wire as set forth in claim 9, wherein a proximal end portion of said distal end side coil and a distal end portion of said proximal end side coil are entangled with each other.

11. A guide wire as set forth in claim 9, wherein said coil is fixed to said coil fixing member through an adhesion material.

12. A guide wire as set forth in claim 9, wherein said coil is fixed to said coil fixing member by welding.

13. A guide wire as set forth in claim 9, wherein said coil fixing member is not a brazed joint, the coil fixing member being connected to said distal end side portion of said core member at a point where the coil fixing member directly overlies the core member to connect said coil with said core member, and said coil being fixed to said coil fixing member by an adhesion material.

14. A guide wire comprising:
a core member having a distal end side portion;
a coil covering at least said distal end side portion of said core member, said coil being formed of a material possessing a melting point;
a fixing member fixed on at least a portion of said distal end side portion of said core member;
said fixing member being a tubular body;
said fixing member being formed at least in part of a material possessing a melting point that is lower than said melting point of said material forming said coil;
said coil being welded to said fixing member to fix the coil to the fixing member at a plurality of spaced-apart melted and solidified portions at which the material forming said coil and the material forming said fixing member have been melted, mixed and solidified, wherein an outside diameter of said distal end side portion of said core member decreases toward a distal end of said guide wire and an inside diameter of said tubular body of said fixing member decreases toward the distal end of said guide wire.

15. A guide wire as set forth in claim 14, wherein said fixing member comprises a distal end portion and a proximal end portion, the distal end portion of the fixing member possessing a smaller outside diameter than the outside diameter of the proximal end portion of the fixing member.

16. A guide wire as set forth in claim 14, wherein said coil is comprised of two portions having different inner diameters.

17. A guide wire as set forth in claim 14, wherein said fixing member is not a brazed joint, and the fixing member being connected to said distal end side portion of said core member at a point where the fixing member directly overlies the core member.

18. The guide wire as set forth in claim 14, wherein the coil comprises a distal end side coil and a proximal end side coil, and the spaced-apart melted and solidified portions are located at the distal end side coil and the proximal end side coil.

19. The guide wire as set forth in claim 14, wherein an outside diameter of a portion of the fixing member is larger than an inside diameter of a portion of the coil in the area of the spaced-apart melted and solidified portion.

20. A guide wire comprising:
a core member having a distal end side portion;
a coil covering at least the distal end side portion of the core member, said coil being formed of a material possessing a melting point;
a fixing member fixed to the distal end side portion of the core member;
the fixing member being a tubular body;
the fixing member being formed at least in part of a material possessing a melting point that is lower than said melting point of the material forming the coil; and
the coil being welded to the fixing member to fix the coil to the coil fixing member at a melted and solidified portion at which the material forming the coil and the material forming the fixing member have been melted, mixed and solidified;
the coil comprising a distal end side coil and a proximal end side coil;
the proximal end portion of the distal end side coil and the distal end portion of the proximal end side coil being entangled with each other at an entangled portion; and
the melted and solidified portion being located at the entangled portion,
wherein an outside diameter of said distal end side portion of said core member decreases toward a distal end of said guide wire and an inside diameter of said tubular body of said fixing member decreases toward the distal end of said guide wire.

* * * * *